United States Patent
Arzeno et al.

(10) Patent No.: US 6,518,276 B2
(45) Date of Patent: Feb. 11, 2003

(54) 7-OXO-PYRIDOPYRIMIDINES (II)

(75) Inventors: Humberto Bartolome Arzeno, Cupertino, CA (US); Jian Jeffrey Chen, Santa Clara, CA (US); James Patrick Dunn, Los Altos, CA (US); David Michael Goldstein, San Jose, CA (US); Julie Anne Lim, San Mateo, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 09/943,338

(22) Filed: Aug. 30, 2001

(65) Prior Publication Data

US 2002/0055513 A1 May 9, 2002

Related U.S. Application Data

(60) Provisional application No. 60/229,584, filed on Aug. 31, 2000, and provisional application No. 60/229,577, filed on Aug. 31, 2000.

(51) Int. Cl.[7] .................... A61K 31/519; C07D 471/04; A61P 11/06; A61P 37/06
(52) U.S. Cl. ................... 514/264.11; 544/279
(58) Field of Search .......... 544/279; 514/258, 514/264.11

(56) References Cited

U.S. PATENT DOCUMENTS

| 5,620,981 A | 4/1997 | Blankley et al. | |
| 5,733,914 A | 3/1998 | Blankley et al. | |
| 5,945,422 A | 8/1999 | Doherty et al. | |
| 2002/0002169 A1 * | 1/2002 | Griffith | 544/279 |

FOREIGN PATENT DOCUMENTS

| WO | WO 96/34867 | 11/1996 |
| WO | WO 96/34867 A1 | 11/1996 |
| WO | WO 02/18380 | 3/2002 |

OTHER PUBLICATIONS

Hele, Respir Res 2001, 2:E003.*
Hingham, Eur Respir J 2000; 15: 281–284.*
Edwards et al, APStracts 5:0150L, Jun. 16, 1998.*

Boehm and Adams, "New inhibitors of p38 kinase," *Expert Opinion on Therapeutic Patents,* vol. 10:1 (2000), pp 25–37.

Trumpp–Kallmeyer, et al., Development of a Binding Model to Protein Tyrosine Kinases for Substituted Pyrido[2,3–d] pyrimidine Inhibitors, *J. Medicinal Chemistry,* vol. 41 (1998), pp 1752–1763.

Klutchko, et al., "2–Substituted Aminopyrido[2,3–d] pyrimidin–7(8H)–ones. Structure–Activity Relationships Against Selected Tyrosine Kinases and in Vitro and in Vivo Anticancer Activity," *J. Medicinal Chemistry,* vol. 41 (1998), pp 3276–3292.

Boschelli, et al., "Synthesis and Tyrosine Kinase Inhibitory Activity of a Series of 2–Amino–8H–pyrido[2,3–d]pyrimidines: Identification of Potent Selective Platelet–Derived Growth Factor Receptor Tyrosine Kinase Inhibitors," *J. Medicinal Chemistry,* vol. 41 (1998), pp 4365–4377.

* cited by examiner

*Primary Examiner*—Mark L. Berch
(74) *Attorney, Agent, or Firm*—Rohan Peries

(57) ABSTRACT

The present invention provides compounds of the formula:

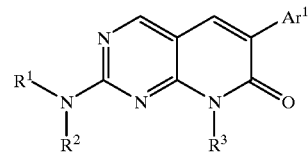

wherein $R^1$, $R^3$, and $Ar^1$ are those defined herein, and $R^2$ is —CR'R"—$R^a$ (where R' and R" are hydrogen, hydroxyalkyl or alkyl with at least one being alkyl or hydroxyalkyl and $R^a$ is hydroxyalkyl), $R^x$—S—$R^y$— (where $R^x$ is alkyl and $R^y$ is alkylene), alkoxy-substituted alkyl, heterocyclylalkyl or $C_4$–$C_5$ cycloalkyl, wherein each of the hydroxy group present in $R^2$ can be independently $R^a$—C(=O)—O, $R^a R^b$N—C(=O)—O, or $R^a$—S(O)$_2$—O—, wherein $R^a$ and $R^b$ are independently hydrogen, alkyl, aryl, or aralkyl, and methods for preparation and uses thereof.

13 Claims, No Drawings

7-OXO-PYRIDOPYRIMIDINES (II)

CROSS-REFERENCE TO RELATED APPLICATIONS

This application claims the benefit of U.S. Provisional Application Nos. 60/229,584, filed Aug. 31, 2000 and 60/229,577, filed Aug. 31, 2000, which are incorporated herein by reference in their entirety. This patent application also incorporates by reference the entire disclosure of U.S. application Ser. No. 09/943,407 entitled 7-Oxo-Pyridopyrimidines (I), filed concurrently herewith on Aug. 30, 2001.

FIELD OF THE INVENTION

The present invention relates to 7-oxo-pyridopyrimidines. In particular, the present invention provides 2,6-disubstituted 7-oxo-pyrido[2,3-d]pyrimidines, a process for their manufacture, pharmaceutical preparations comprising the same, and methods for using the same.

BACKGROUND OF THE INVENTION

Mitogen-activated protein kinases (MAP) is a family of proline-directed serine/threonine kinases that activate their substrates by dual phosphorylation. The kinases are activated by a variety of signals including nutritional and osmotic stress, UV light, growth factors, endotoxin and inflammatory cytokines. One group of MAP kinases is the p38 kinase group which includes various isoforms (e.g., p38α, p39β, p38γ and p38δ). The p38 kinases are responsible for phosphorylating and activating transcription factors as well as other kinases, and are activated by physical and chemical stress, pro-inflammatory cytokines and bacterial lipopolysaccharide.

More importantly, the products of the p38 phosphorylation have been shown to mediate the production of inflammatory cytokines, including TNF and IL-1, and cyclooxygenase-2. Each of these cytokines has been implicated in numerous disease states and conditions. For example, TNF-α is a cytokine produced primarily by activated monocytes and macrophages. Its excessive or unregulated production has been implicated as playing a causative role in the pathogenesis of rheumatoid arthritis. More recently, inhibition of TNF production has been shown to have broad application in the treatment of inflammation, inflammatory bowel disease, multiple sclerosis and asthma.

TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpesvirus-7 (HHV-7), human herpesvirus-8 (HHV-8), pseudorabies and rhinotracheitis, among others.

Similarly, IL-1 is produced by activated monocytes and macrophages, and plays a role in many pathophysiological responses including rheumatoid arthritis, fever and reduction of bone resorption.

Additionally, the involvement of p38 has been implicated in stroke, Alzheimer's disease, osteoarthritis, lung injury, septic shock, angiogenesis, dermatitis, psoriasis and atopic dermatitis. *J. Exp. Opin. Ther. Patents*, (2000) 10(1).

Certain pyrido[2,3-d]pyrimidines are disclosed as inhibitors of protein tyrosine kinase mediated cellular proliferation in WO 96/34867, published Nov. 7, 1996 (Warner Lambert).

The inhibition of these cytokines by inhibition of the p38 kinase is of benefit in controlling, reducing and alleviating many of these disease states.

SUMMARY OF THE INVENTION

One aspect of the present invention provides compounds represented by the Formula:

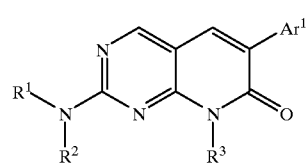

I a prodrug or a pharmaceutically acceptable salt thereof, in which:

$R^1$ is hydrogen or alkyl;

$R^2$ is —CR'R"—$R^a$ (where R' and R" are hydrogen, hydroxyalkyl or alkyl with at least one being alkyl or hydroxyalkyl and $R^a$ is hydroxyalkyl), $R^x$—S—$R^y$—(where $R^x$ is alkyl and $R^y$ is alkylene), alkoxy-substituted alkyl, heterocyclylalkyl or $C_4$–$C_5$ cycloalkyl, wherein each of the hydroxy group present in $R^2$ can be independently in the form of an ester, a carbamate, a carbonate, or a sulfonate derivative; or $R^1$ and $R^2$ together with the nitrogen atom to which they are attached form aheterocyclyl group;

$R^3$ is hydrogen, alkyl, cycloalkyl, aryl, aralkyl, haloalkyl, heteroalkyl, cyanoalkyl, amino, monoalkylamino, dialkylamino, alkylene-C(O)—R (where R is hydrogen, alkyl, hydroxy, alkoxy, amino, monoalkylamino or dialkylamino) or acyl; and $Ar^1$ is aryl.

The compounds of Formula I and their aforementioned salts are inhibitors of protein kinases, and exhibit effective activity against p38 in vivo. Therefore, the compounds can be used for the treatment of diseases mediated by the pro-inflammatory cytokines such as TNF and IL-1.

Thus, another aspect of the present invention provides methods for the treatment of p38 mediated diseases or conditions in which a therapeutically effective amount of a compound of Formula I is administered to a patient in need of such treatment.

Yet another aspect of the present invention provides methods for preparing the compounds described above.

Still yet another aspect of the present invention provides methods for preparing medicaments useful for the treatment of the p38 mediated diseases and conditions.

DEFINITIONS

Unless otherwise stated, the following terms used in the specification and claims have the meanings given below:

"Acyl" means a radical —C(O)R, where R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formyl, acetyl, cylcohexylcarbonyl, cyclohexylmethylcarbonyl, benzoyl, benzylcarbonyl, and the like.

"Acylamino" means a radical —NR'C(O)R, where R' is hydrogen or alkyl, and R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formylamino, acetylamino, cylcohexylcarbonylamino, cyclohexylmethyl-carbonylamino, benzoylamino, benzylcarbonylamino, and the like.

"Alkoxy" means a radical —OR where R is an alkyl as defined herein e.g., methoxy, ethoxy, propoxy, butoxy and the like.

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, n-butyl, iso-butyl, tert-butyl, pentyl, and the like. "Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkylthio" means a radical —SR where R is an alkyl as defined above e.g., methylthio, ethylthio, propylthio, butylthio, and the like.

"Aryl" means a monovalent monocyclic or bicyclic aromatic hydrocarbon radical which is optionally substituted independently with one or more substituents, preferably one, two or three, substituents preferably selected from the group consisting of alkyl, hydroxy, alkoxy, haloalkyl, haloalkoxy, heteroalkyl, halo, nitro, cyano, amino, monoalkylamino, dialkylamino, methylenedioxy, ethylenedioxy and acyl. More specifically the term aryl includes, but is not limited to, phenyl, chlorophenyl, fluorophenyl, methoxyphenyl, 1-naphthyl, 2-naphthyl, and the derivatives thereof.

"Cycloalkyl" refers to a saturated monovalent cyclic hydrocarbon radical of three to seven ring carbons e.g., cyclopropyl, cyclobutyl, cyclohexyl, 4-methylcyclohexyl, and the like.

"Cycloalkylalkyl" means a radical —$R^a R^b$ where $R^a$ is an alkylene group and $R^b$ is cycloalkyl group as defined herein, e.g., cyclohexylmethyl, and the like.

"Dialkylamino" means a radical —NRR' where R and R' independently represent an alkyl, hydroxyalkyl, cycloalkyl, or cycloalkylalkyl group as defined herein. Representative examples include, but are not limited to dimethylamino, methylethylamino, di(1-methylethyl)amino, (cyclohexyl)(methyl)amino, (cyclohexyl)(ethyl)amino, (cyclohexyl)(propyl)amino, (cyclohexylmethyl)(methyl)amino, (cyclohexylmethyl)(ethyl)amino, and the like.

The term "each of the hydroxy group present in $R^2$ can be independently in the form of an ester, a carbamate, a carbonate or a sulfonate derivative" means that hydroxy group(s) (—OH) which are present in the $R^2$ group can be independently derivatized as $R^a$—C(=O)—O—, $R^a R^b$N—C(=O)—O—, $R^a$—O—C(=O)—O— or $R^a$—$SO_2$—O—, respectively, where $R^a$ and $R^b$ is independently hydrogen, alkyl, aryl or aralkyl as defined herein.

"Halo" means fluoro, chloro, bromo, or iodo, preferably fluoro and chloro.

"Haloalkyl" means alkyl substituted with one or more same or different halo atoms, e.g., —$CH_2Cl$, —$CF_3$, —$CH_2CF_3$, —$CH_2CCl_3$, and the like.

"Heteroalkyl" means an alkyl radical as defined herein wherein one, two or three hydrogen atoms have been replaced with a substituent independently selected from the group consisting of —$OR^a$, —$NR^b R^c$, and —$S(O)_n R^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl, or $R^b$ and $R^c$ together forms cycloalkyl or arylcycloalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroalkylsubstituted cycloalkyl" means a cycloalkyl radical as defined herein wherein one, two or three hydrogen atoms in the cycloalkyl radical have been replaced with a heteroalkyl group with the understanding that the heteroalkyl radical is attached to the cycloalkyl radical via a carbon—carbon bond. Representative examples include, but are not limited to, 1-hydroxymethylcyclopentyl, 2-hydroxymethylcyclohexyl, and the like.

"Heterosubstituted cycloalkyl" means a cycloalkyl radical as defined herein wherein one, two or three hydrogen atoms in the cycloalkyl radical have been replaced with a substituent independently selected from the group consisting of hydroxy, alkoxy, amino, acylamino, monoalkylamino, dialkylamino, oxo (C=O), imino, hydroximino (=NOH), $NR'SO_2R^d$ (where R' is hydrogen or alkyl and $R^d$ is alkyl, cycloalkyl, amino, monoalkylamino or dialkylamino), —X—C(O)R (where X is O or NR', R is hydrogen, alkyl, haloalkyl, alkoxy, amino, monoalkylamino, dialkylamino, or optionally substituted phenyl, and R' is H or alkyl), or —$S(O)_n R$ (where n is an integer from 0 to 2) such that when n is 0, R is hydrogen, alkyl, cycloalkyl, or cycloalkylalkyl, and when n is 1 or 2, R is alkyl, cycloalkyl, cycloalkylalkyl, amino, acylamino, monoalkylamino or dialkylamino. Representative examples include, but are not limited to, 2-, 3-, or 4-hydroxycyclohexyl, 2-, 3-, or 4-aminocyclohexyl, 2-, 3-, or 4-methanesulfonamido-cyclohexyl, and the like, preferably 4-hydroxycyclohexyl, 2-aminocyclohexyl, 4-methanesulfonamido-cyclohexyl.

"Heterosubstituted cycloalkyl-alkyl" means a radical $R^a R^b$— where $R^a$ is a heterosubstituted cycloalkyl radical and $R^b$ is an alkylene radical.

"Heterocyclyl" means a saturated or unsaturated non-aromatic cyclic radical of 3 to 8 ring atoms in which one or two ring atoms are heteroatoms selected from N, O, or $S(O)_n$ (where n is an integer from 0 to 2), the remaining ring atoms being C. The heterocyclyl ring may be optionally substituted independently with one, two, three or four substituents selected from alkyl, haloalkyl, heteroalkyl, halo, nitro, cyano, cyanoalkyl, hydroxy, alkoxy, amino, monoalkylamino, dialkylamino, aralkyl, —$(X)_n$—C(O)R (where, X is O or NR', n is 0 or 1, R is hydrogen, alkyl, haloalkyl, hydroxy (when n is 0), alkoxy, amino, monoalkylamino, dialkylamino or optionally substituted phenyl, and R' is H or alkyl), -alkylene-C(O)R (where R is OR or NR'R" and R is hydrogen, alkyl or haloalkyl, and R' and R" are independently hydrogen or alkyl), -alkylene-S(O)_n—$R^a$ (where n is 0, 1 or 2, preferably 0, and $R^a$ is alkyl) or —$S(O)_n R$ (where n is an integer from 0 to 2) such that when n is 0, R is hydrogen, alkyl, haloalkyl, cycloalkyl, or cycloalkylalkyl, and when n is 1 or 2, R is alkyl, cycloalkyl, cycloalkylalkyl, amino, acylamino, monoalkylamino or dialkylamino. More specifically the term heterocyclyl includes, but is not limited to, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, pyrrolinyl, imidazolinyl, N-methanesulfonyl-piperidin-4-yl, and the derivatives thereof. "Heterocyclylalkyl" means a radical —$R^a$ $R^b$ where $R^a$ is an alkylene group and $R^b$ is a heterocyclyl group as defined above with the understanding that $R^b$ is attached to $R^a$ via a carbon atom of the heterocyclyl ring, e.g., tetrahydropyran-2-ylmethyl, 2- or 3-piperidinylmethyl, and the like.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl, preferably 2-hydroxyethyl, 2,3-dihydroxypropyl and 1-(hydroxymethyl)-2-hydroxyethyl. Accordingly, as used herein, the term "hydroxyalkyl" is used to define a subset of heteroalkyl groups.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Monoalkylamino" means a radical —NHR where R is an alkyl, hydroxyalkyl, cycloalkyl, or cycloalkylalkyl group as defined above, e.g., methylamino, (1-methylethyl)amino, hydroxymethylamino, cyclohexylamino, cyclohexylmethylamino, cyclohexylethylamino, and the like.

"Optionally substituted phenyl" means a phenyl ring which is optionally substituted independently with one or more substituents, preferably one or two substituents selected from the group consisting of alkyl, hydroxy, alkoxy, haloalkyl, haloalkoxy, heteroalkyl, halo, nitro, cyano, amino, methylenedioxy, ethylenedioxy, and acyl.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, sulfhydryl, carboxy or carbonyl group in a compound of Formula I is bonded to any group that may be cleaved in vivo to regenerate the free hydroxyl, amino, or sulfhydryl group, respectively. Examples of prodrugs include, but are not limited to, esters (e.g., acetate, dialkylaminoacetates, formates, phosphates, sulfates, and benzoate derivatives), sulfonates and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p1–92, Elesevier, New York-Oxford (1985).

"Protecting group" refers to a grouping of atoms that when attached to a reactive group in a molecule masks, reduces or prevents that reactivity. Examples of protecting groups can be found in T. W. Green and P. G. Futs, *Protective Groups in Organic Chemistry*, (Wiley, 2$^{nd}$ ed. 1991) and Harrison and Harrison et al., *Compendium of Synthetic Organic Methods*, Vols. 1–8 (John Wiley and Sons, 1971–1996). Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "treating", "contacting" or "reacting" when referring to a chemical reaction, means to add or mix two or more reagents under appropriate conditions to produce the indicated and/or the desired product. It should be appreciated that the reaction which produces the indicated and/or the desired product may not necessarily result directly from the combination of two reagents which were initially added, i.e., there can be one or more intermediates which are produced in the mixture which ultimately leads to the formation of the indicated and/or the desired product.

DETAILED DESCRIPTION

One aspect of the present invention provides compounds represented by the formula:

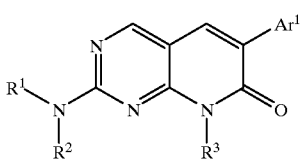

I where:

R$^1$ is hydrogen or alkyl;

R$^2$ is —CR'R"—R$^a$ (where R' and R" are hydrogen or alkyl with at least one being alkyl and R$^a$ is hydroxyalkyl), dihydroxyalkyl, R$^x$—S—R$^y$— (where R$^x$ is alkyl and R$^y$ is alkylene), alkoxy-substituted alkyl, heterocyclylalkyl or C$_4$-C$_5$ cycloalkyl, wherein each of the hydroxy group present in R$^2$ can be independently in the form of an ester, a carbamate, a carbonate, or a sulfonate derivative; or R$^1$ and R$^2$ together with the nitrogen atom to which they are attached form a heterocyclyl group;

R$^3$ is hydrogen, alkyl, cycloalkyl, aryl, aralkyl, haloalkyl, heteroalkyl, cyanoalkyl, alkylene-C(O)—R (where R is hydrogen, alkyl, hydroxy, alkoxy, amino, monoalkylamino or dialkylamino) or acyl; and Ar$^1$ is aryl.

Particularly preferred compounds of Formula I are those represented by the Formula II:

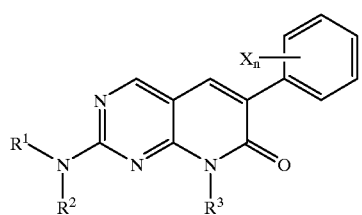

II where n is 1 or 2 and X is hydrogen, alkyl, halo, nitro, cyano or methoxy

More preferred compounds of Formula I are those represented by the Formula III:

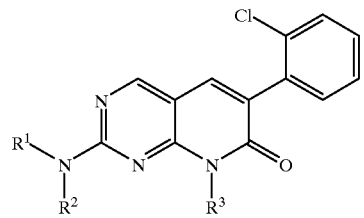

III

In reference to compounds of Formula I:

Preferably, R$^1$ is hydrogen or methyl. More preferably, R$^1$ is hydrogen.

Preferably, R$^2$ of compounds of Formula I is —CR'R"—R$^a$ (where R' and R" are hydrogen, hydroxyalkyl or alkyl with at least one being alkyl or hydroxyalkyl and R$^a$ is hydroxyalkyl), alkoxy-substituted alkyl, or (N-substituted piperidin-4-yl)methyl, wherein each of the hydroxy group present in R$^2$ can be independently in the form of an ester, a carbamate, a carbonate, or a sulfonate derivative. More preferably R$^2$ is (1,1-dimethyl-2-hydroxy)ethyl, (1,2-dimethyl-2-hydroxy)propyl, (N-methyl piperidin-4-yl)methyl, [1-dimethylacetamido-piperidin-4-yl]methyl, [1-carboxymethyl-piperidin-4-yl]methyl, (1,1-dimethyl-2-hydroxy)ethyl, (1-methyl-3-hydroxy)propyl, (1-methyl-1-hydroxymethyl-2-hydroxy)ethyl, [1,1-di(hydroxymethyl)]propyl, (1-hydroxymethyl-2-methyl)propyl, (1-hydroxymethyl)propyl, (1-hydroxymethyl-2,2-dimethyl)propyl, (1-hydroxymethyl-3-methyl)butyl, (2-hydroxy)propyl, (1-methyl-2-hydroxy)ethyl, (1-hydroxymethyl-2-methyl)butyl, 2-hydroxyethyl, 2-hydroxy-2-methylpropyl, 5-hydroxypentyl, 2-hydroxybutyl, 1-(hydroxymethyl)-2-hydroxyethyl, 2,3-dihydroxypropyl or [1-carbomethoxymethyl-piperidin-4-yl]methyl, wherein each of the hydroxy group present in R$^2$ can be independently in the form of an ester, a carbamate, a carbonate, or a sulfonate derivative.

In another embodiment, preferably R$^1$ and R$^2$ together with the nitrogen atom to which they are attached form -alkylene-S(O)$_n$ —R$^a$— substituted heterocyclyl (where n is 0, 1 or 2, preferably 0, and R$^a$ is alkyl). More preferably, R$^1$ and R$^2$ together with the nitrogen atom to which they are attached form -alkylene-S(O)$_n$—R$^a$— substituted aziridinyl.

Preferably, R$^3$ of compounds of Formula I is alkyl, amino, monoalkylamino, dialkylamino, haloalkyl, cycloalkyl, cyanomethyl, heteroalkyl, aryl, aralkyl or alkylene-C(O)—R (where R is hydrogen, alkyl, hydroxy, alkoxy, amino, monoalkylamino or dialkylamino). Most preferably R$^3$ is amino, methyl, 2,2,2-trifluoroethyl, cyclopropyl, cyanomethyl, 2-hydroxyethyl, 4-fluorophenyl, benzyl, carboxymethyl or methoxycarbonylmethyl. Even more preferably, R$^3$ is methyl.

It should be appreciated that when R$^3$ is hydrogen, the compounds can exist in tautomeric form as follows:

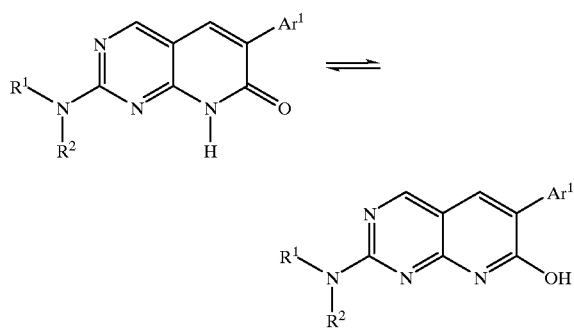

Thus, in addition to the compounds described above, the present invention includes all tautomeric forms. Furthermore, the present invention also includes all pharmaceutically acceptable salts of those compounds along with prodrug forms of the compounds and all stereoisomers whether in a pure chiral form or a racemic mixture or other form of mixture.

Still further, combinations of the preferred groups described above will form other preferred embodiments; thus, for example, preferred substituents $R^1$, $R^2$ and $R^3$ of Formula I are also preferred substituents of compounds of Formulas II and III.

Some of the representative compounds of Formula I are shown in Table 1 below.

TABLE 1

Representative compounds of Formula I

| Cpd # | STRUCTURE | Melting Point (° C.) | Mass spec (MH+) |
|---|---|---|---|
| 1 | 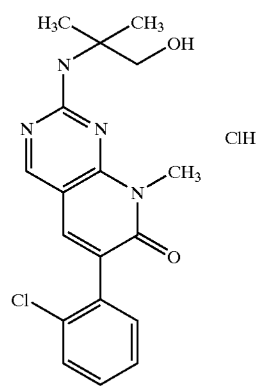 | 228.6–228.9 (salt) | 358 |
| 2 | 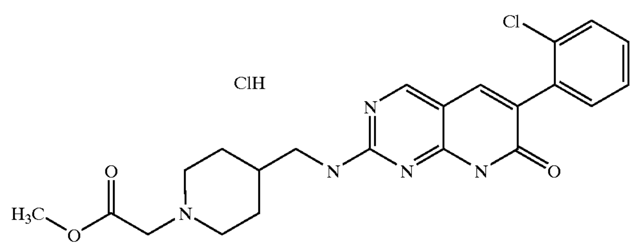 | 220–221.1 (salt) | 442 |
| 3 | 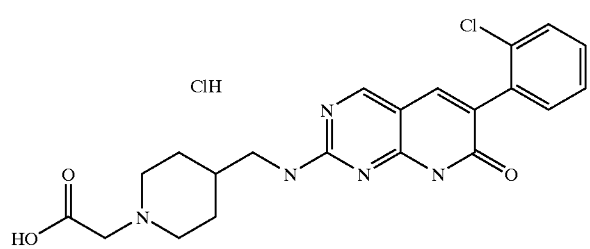 | 235.3–237.9 (salt) | 428 |

TABLE 1-continued

Representative compounds of Formula I

| Cpd # | STRUCTURE | Melting Point (° C.) | Mass spec (MH+) |
|---|---|---|---|
| 4 | 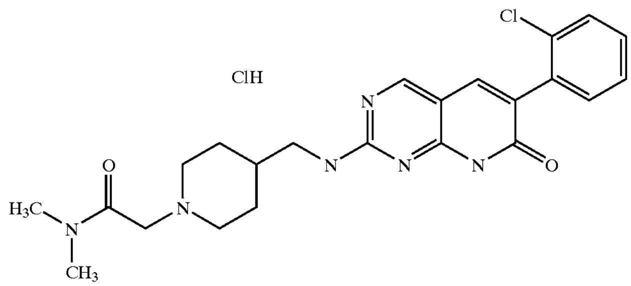 | 211.8–212.8 (salt) | 455 |
| 5 | 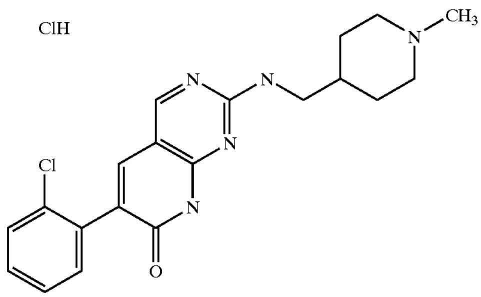 | 213–220 (salt) | 383 |
| 6 | 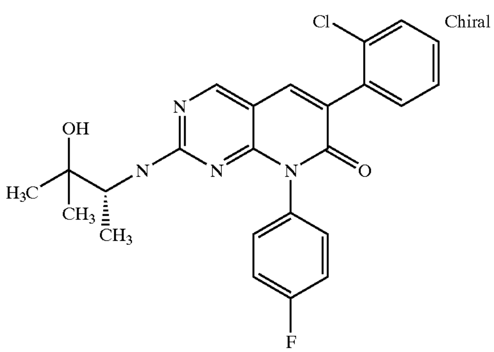 | 206.8–207.5 | 453 |
| 7 | 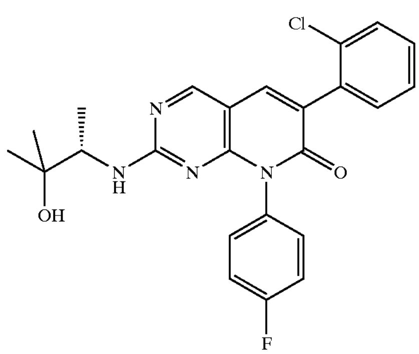 | 142.0–149.0 | 453 |
| 8 | 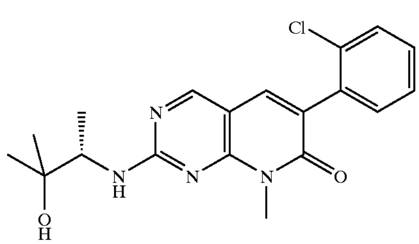 | 178.0–181.5 | 373 |

TABLE 1-continued

Representative compounds of Formula I

| Cpd # | STRUCTURE | Melting Point (° C.) | Mass spec (MH+) |
|---|---|---|---|
| 9 | 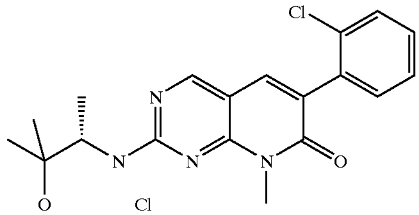 | 194–195.3 | 373 |
| 10 | 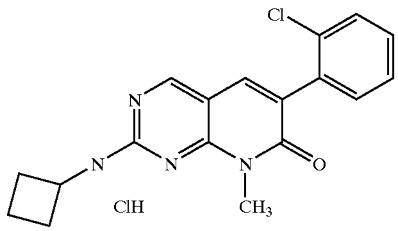 | 205.3–210.9 | |
| 11 | 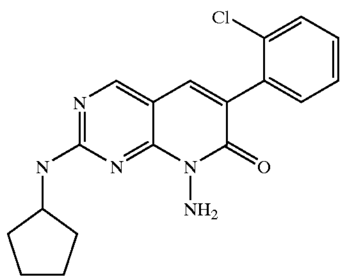 | 147–154 | |
| 12 | 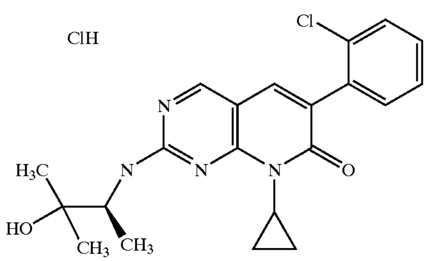 | | 436.36 |
| 13 | 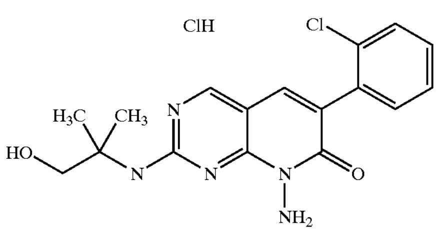 | 145.0–163.0 | |
| 14 | 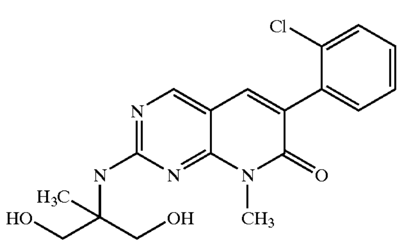 | 200.0–210.0 | 374 |

TABLE 1-continued
Representative compounds of Formula I
| Cpd # | STRUCTURE | Melting Point (° C.) | Mass spec (MH+) |
|---|---|---|---|
| 15 | 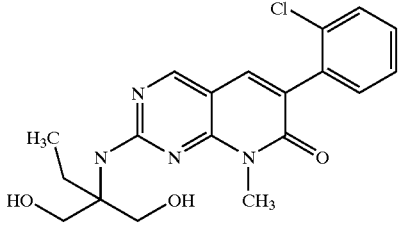 | 98.1–102.0 | 388 |
| 16 | 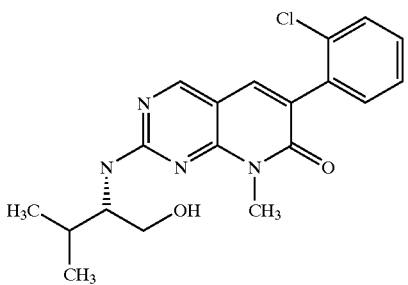 | 167.1–169.1 | 372 |
| 17 | 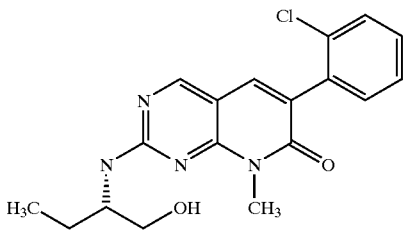 | 170.5–172.1 | 358 |
| 18 | 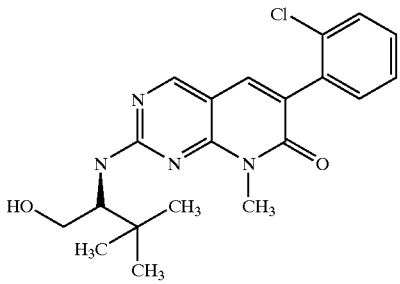 | 171.2–174.0 | 386 |
| 19 | 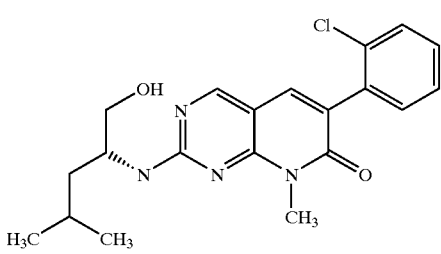 | 173.1–176.2 | 386 |
| 20 | 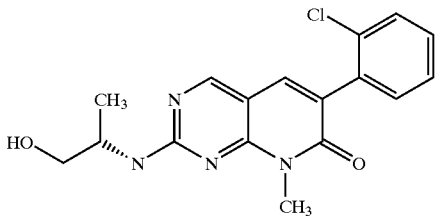 | 131.1–132.2 | 344 |

TABLE 1-continued

Representative compounds of Formula I

| Cpd # | STRUCTURE | Melting Point (° C.) | Mass spec (MH+) |
|---|---|---|---|
| 21 | 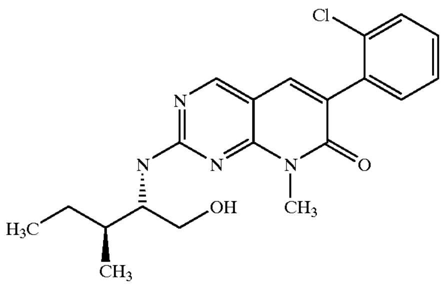 | 140.1–143.6 | 386 |
| 22 | 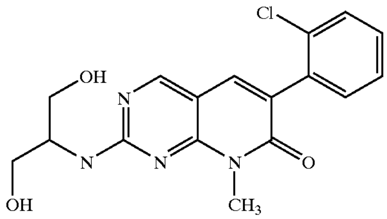 | 155.8–157.3 | 360 |
| 23 | 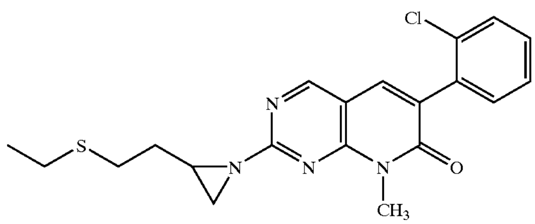 | | 403 |
| 24 | 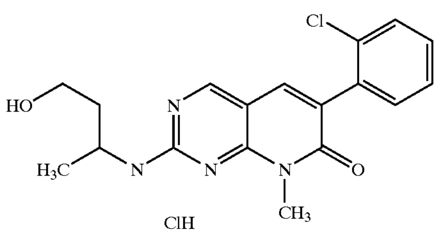 | 180.7–189.2 | |
| 25 | 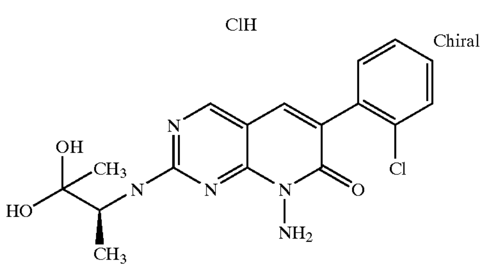 | >300 | |
| 26 | 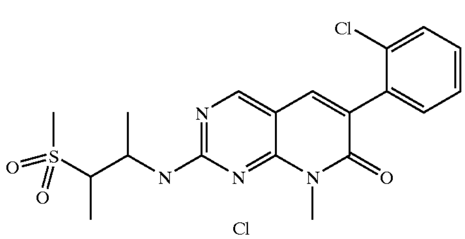 | 142.1–144.3 | |

TABLE 1-continued

Representative compounds of Formula I

| Cpd # | STRUCTURE | Melting Point (° C.) | Mass spec (MH+) |
|---|---|---|---|
| 27 | 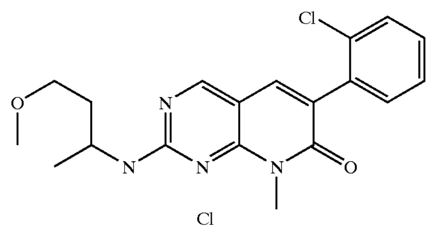 | 156.4–160.2 | |
| 28 | 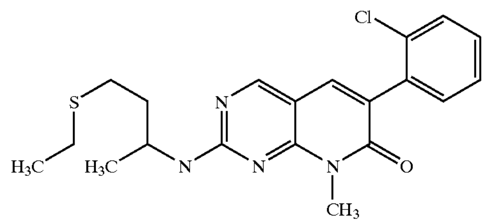 | | 403 |

The IC$_{50}$ of Compounds of Formula I in the in vitro p38 assay is less than 10 μM, preferably less than 5 μM, more preferably less than 2 μM, and most preferably less than 1 μM. In particular, Compounds of Formula I in Table I have IC$_{50}$ in the in vitro p38 assay of from about 0.712 μM to about 0.001 μM.

The compounds of the present invention can exist in unsolvated forms as well as solvated forms, including hydrated forms. In general, the solvated forms, including hydrated forms, are equivalent to unsolvated forms and are intended to be encompassed within the scope of the present invention. Furthermore, as stated above, the present invention also includes all pharmaceutically acceptable salts of those compounds along with prodrug forms of the compounds and all stereoisomers whether in a pure chiral form or a racemic mixture or other form of mixture.

The compounds of Formula I are capable of further forming pharmaceutically acceptable acid addition salts. All of these forms are within the scope of the present invention.

Pharmaceutically acceptable acid addition salts of the compounds of Formula I include salts derived from inorganic acids such as hydrochloric, nitric, phosphoric, sulfuric, hydrobromic, hydriodic, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge et al., "Pharmaceutical Salts," *J. of Pharmaceutical Science*, 1977, 66, 1–19).

The acid addition salts of the basic compounds can be prepared by contacting the free base form with a sufficient amount of the desired acid to produce the salt in the conventional manner. The free base form can be regenerated by contacting the salt form with a base and isolating the free base in the conventional manner. The free base forms may differ from their respective salt forms somewhat in certain physical properties such as solubility in polar solvents, but otherwise the salts are equivalent to their respective free base for purposes of the present invention.

Pharmaceutically acceptable base addition salts can be formed with metal ions or amines, such as alkali and alkaline earth metal ions or organic amines. Examples of metal ions which are used as cations include sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge et al, "Pharmaceutical Salts," *J. of Pharmaceutical Science*, 1977, 66, 1–19).

The base addition salts of acidic compounds can be prepared by contacting the free acid form with a sufficient amount of the desired base to produce the salt in the conventional manner. The free acid form can be regenerated by contacting the salt form with an acid and isolating the free acid in the conventional manner. The free acid forms may differ from their respective salt forms somewhat in certain physical properties such as solubility in polar solvents, but otherwise the salts are equivalent to their respective free acid for purposes of the present invention.

Processes for Preparing the Compounds

The compounds of the present invention can be prepared by a variety of methods, using procedures well known to those of skill in the art. In one aspect of the present invention, a method for preparing compounds of Formula I is shown in Scheme 1 below.

Scheme 1

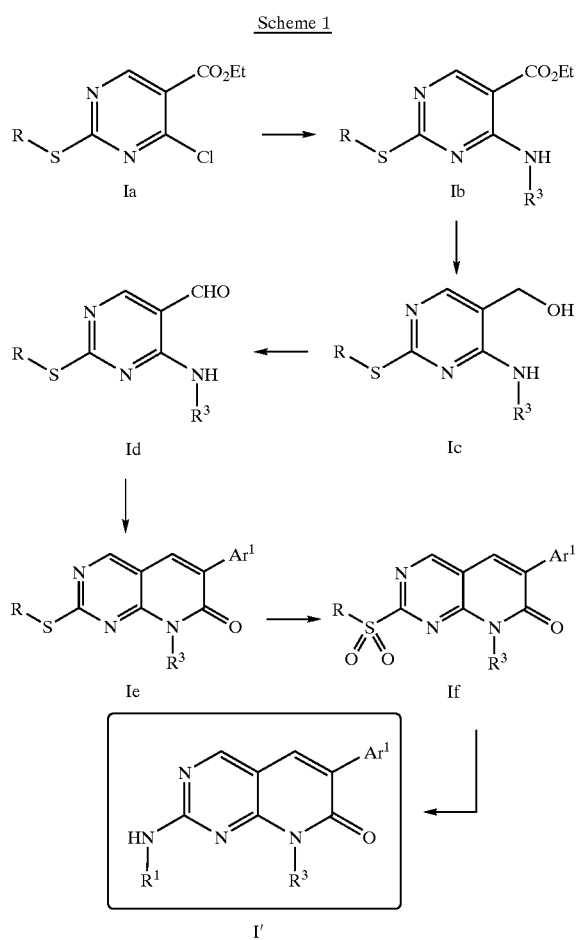

Treatment of a compound of Formula Ia with a primary amine ($R^3$—$NH_2$) provides a compound of Formula Ib. This reaction is conveniently carried out in a solvent which is inert under the reaction conditions, preferably a halogenated aliphatic hydrocarbon, especially dichloromethane, an optionally halogenated aromatic hydrocarbon, an open-chain or cyclic ether (e.g. tetrahydrofuran), a formamide or a lower alkanol. Suitably, the reaction is carried out at about −20° C. to about 120° C.

Reduction of a compound of Formula Ib provides an alcohol of Formula Ic. This reduction is typically carried out using lithium aluminum hydride in a manner well known to those of skill in the art (e.g., in a solvent which is inert under the conditions of the reduction, preferably an open-chain or cyclic ether, especially tetrahydrofuran, at about −20° C. to about 70° C., preferably at about 0° C. to about room temperature).

Oxidation of an alcohol of Formula Ic in the next step provides a carboxaldehyde of Formula Id. The oxidation is typically carried out with manganese dioxide, although numerous other methods can also be employed (see, for example, ADVANCED ORGANIC CHEMISTRY, 4$^{TH}$ ED., March, John Wiley & Sons, New York (1992)). Depending on the oxidizing agent employed, the reaction is carried out conveniently in a solvent which is inert under the specific oxidation conditions, preferably a halogenated aliphatic hydrocarbon, especially dichloromethane, or an optionally halogenated aromatic hydrocarbon. Suitably, the oxidation is carried out at about 0° C. to about 60° C.

Reaction of a carboxaldehyde of Formula Id with an aryl substituted acetate $Ar^1$—$CH_2$—$CO_2R$ (where R is an alkyl group) in a presence of a base provides a compound of Formula Ie. Any relatively non-nucleophilic base can be used including carbonates, such as potassium carbonate, lithium carbonate, and sodium carbonate; bicarbonates, such as potassium bicarbonate, lithium bicarbonate, and sodium bicarbonate; amines, such as secondary and tertiary amines; and resin bound amines such as 1,3,4,6,7,8-hexahydro-2H pyrimido[1,2-a]pyrimidine. To increase the product yield and/or to increase the reaction rate, water which is formed in the reaction can be removed by azeotrope. Conveniently, the reaction is carried out in a solvent which is relatively polar but inert under the reaction conditions, preferably an amide such as dimethyl formamide, N-substituted pyrrolidinone, especially 1-methyl-2-pyrrolidinone, and at a temperature of about 70° C. to about 150° C., especially at or near the reflux temperature of the solvent to assist in the noted azeotropic removal of water.

Oxidation of Ie with an oxidizing agent, such as 3-chloroperbenzoic acid (i.e., MCPBA) and Oxone® provides a sulfone (If) which can be converted to a variety of target compounds. Typically the oxidation of Ie is carried out in a solvent which is inert under the conditions of the oxidation. For example, when MCPBA is used as the oxidizing agent, the solvent is preferably a halogenated aliphatic hydrocarbon, especially chloroform. When Oxone® is used as the oxidizing agent, the solvent can be water or a mixture of an organic solvent (such as acetonitrile) and water. The reaction temperature depends on the solvent used. For an organic solvent, the reaction temperature is generally at about −20° C. to about 50° C., preferably about 0° C. to about room temperature. When water is used as the solvent, the reaction temperature is generally from about 0° C. to about 50° C., preferably about 0° C. to about room temperature. Alternatively, the oxidation can be carried under catalytic conditions with rhenium/peroxide based reagents. See, for example, "Oxidation of Sulfoxides by Hydrogen Peroxide, Catalyzed by Methyltrioxorhenium(VII)", Lahti, David W.; Espenson, James H, *Inorg. Chem.* 2000, 39(10) pp.2164–2167; "Rhenium oxo complexes in catalytic oxidations," *Catal. Today,* 2000, 55(4), pp317–363 and "A Simple and Efficient Method for the Preparation of Pyridine N-Oxides", Coperet, Christophe; Adolfsson, Hans; Khuong, Tinh-Alfredo V.; Yudin, Andrei K.; Sharpless, K. Barry, *J. Org. Chem.*, 1998, 63(5), pp1740–1741, which are incorporated herein by reference in their entirety.

Reaction of the compound If with an amine ($R^2$—$NH_2$) provides the compounds of Formula I' (i.e. compounds I, wherein $R^1$ is hydrogen). Further alkylation of I' then provides compounds of Formula I, where $R^1$ is not hydrogen. The reaction can be carried out in the presence or absence of solvent. Conveniently, the reaction is carried out at temperatures of from about 0° C. to about 200° C., more preferably about room temperature to about 150° C. Alternatively, in some cases rather than using the sulfone If, the sulfide Ie or the corresponding sulfoxide can be reacted directly an amine ($R^1$—$NH_2$) to provide the compounds of Formula I'. Furthermore, If can also be alkylated with an amine of $R^1R^2NH$ directly to provide a compound of Formula I where $R^1$ and $R^2$ are as described in the Summary of the Invention.

Accordingly, the present invention provides a method of preparing compounds of Formula I, by treating a compound of general Formula Ie or If with an amine ($R^1$—$NH_2$) and optionally reacting the resulting product with $R^1$—L, where $R^1$ is defined above, but excludes hydrogen, and L is a leaving group.

Alternatively, the carboxaldehyde of the Compound of Formula Ie can be prepared as shown in Scheme II below, which eliminates a need for an ester reduction and an alcohol oxidation in Scheme I.

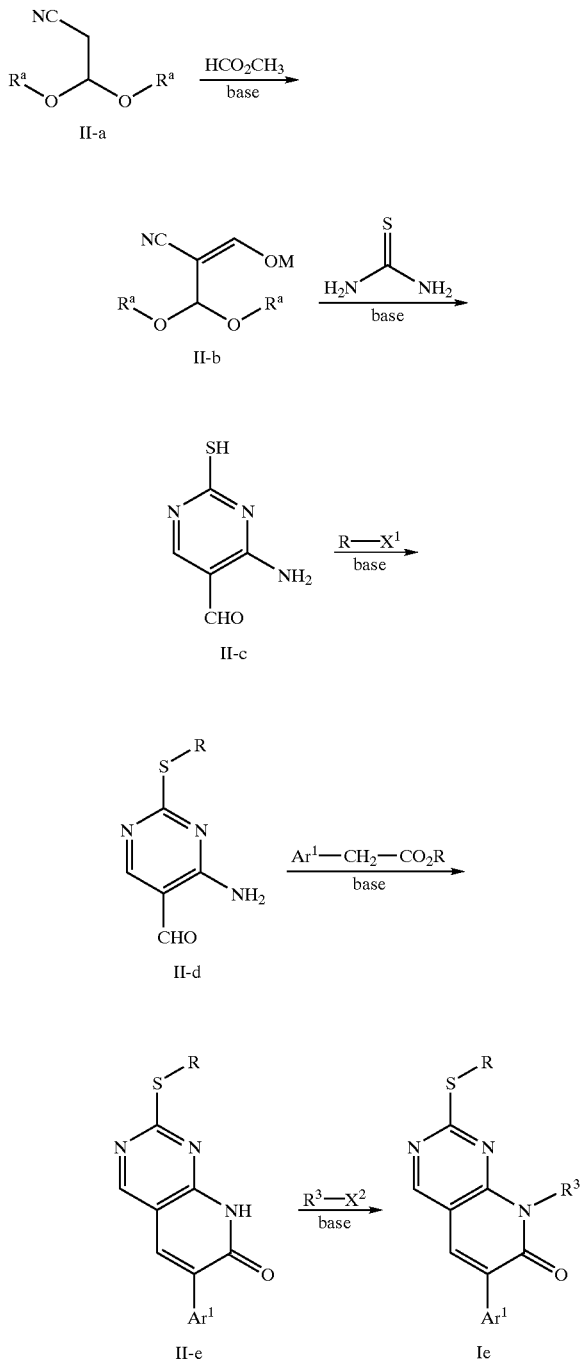

Scheme II

Treatment of a compound of Formula II-a (where each $R^a$ is independently alkyl) with an alkyl formate (e.g., methylformate) in the presence of a base provides a compound of Formula II-b (where M is a metal). This reaction is conveniently carried out at a temperature range of from about 0° C. to about 100° C. Typically, an ether, such as THF, and other solvents which are inert to the reaction conditions is used. Suitable bases include alkoxides, such as tert-butoxides, and other relatively non-nucleophilic bases that are capable of deprotonating the compound of Formula II-a.

Cyclization of a compound of Formula II-b with thiourea in the presence of a base affords a pyrimidine of Formula II-c. Typically, this cyclization reaction is conducted in an alcoholic solvent under refluxing conditions using a corresponding alkoxide as a base.

Alkylation of a compound of Formula II-c with an alkylating agent $R-X^1$ (where R is an alkyl group and $X^1$ is a leaving group, such as halide) in the presence of a base then provides a compound of Formula II-d. Suitable bases include a relatively non-nucleophilic bases including carbonates, such as potassium carbonate, lithium carbonate, and sodium carbonate; and bicarbonates, such as potassium bicarbonate, lithium bicarbonate, and sodium bicarbonate. Conveniently, the reaction is carried out in a relatively polar solvent that inert under the reaction conditions, preferably acetone, dimethylformamide (DMF) or methylpyrrolidinone (MP).

Reaction of a compound of Formula II-d with an aryl substituted acetate $Ar^1-CH_2-CO_2R$ (where R is an alkyl group) under similar conditions as that described for preparation of a compound of Formula Ie in Scheme I above, then provides a compound of Formula II-e. While the alkylation of a compound of Formula II-c is generally conducted prior to the reaction with an aryl substituted acetate, the order of these two reactions are not crucial and can be reversed. Thus, a compound of Formula II-c can be reacted with an aryl substituted acetate $Ar^1-CH_2-CO_2R$ and the resulting product can be alkylated with an alkylating agent $R-X^1$ to provide a compound of Formula II-e.

Alkylation of the amine group of a compound of Formula II-e with an alkylating agent $R^3-X^2$ (where $R^3$ is those defined above and $X^2$ is a leaving group, such as halide) then provides a compound of Ie which can be further converted to a compound of Formula I' as described in Scheme I.

Thus, another aspect of the present invention provides a method of preparing a pyrimidine compound of Formula II-c by reacting an acetal of the Formula II-a with an alkyl formate and reacting the resulting product with a thiourea.

Yet another aspect of the present invention provides a method for preparing a compound of Formula II-e, by reacting a compound of Formula II-c with an alkylating agent or an aryl substituted acetate, and reacting the resulting product with an aryl substituted acetate or an alkylating agent, respectively.

One of skill in the art will understand that certain modifications to the above schemes are contemplated and within the scope of the present invention. For example, certain steps will involve the use of protecting groups for functional groups that are not compatible with particular reaction conditions.

Pharmaceutical Compositions Containing the Compounds

The compounds of Formula I and the pharmaceutically acceptable salts of basic compounds of Formula I with acids can be used as medicaments, e.g., in the form of pharmaceutical preparations. The pharmaceutical preparations can be administered enterally, e.g., orally in the form of tablets, coated tablets, dragées, hard and soft gelatine capsules, solutions, emulsions or suspensions, nasally, e.g., in the form of nasal sprays, or rectally, e.g., in the form of suppositories. However, they may also be administered parenterally, e.g., in the form of injection solutions.

The compounds of Formula I and their aforementioned pharmaceutically acceptable salts can be processed with pharmaceutically inert, organic or inorganic carriers for the production of pharmaceutical preparations. Lactose, corn starch or derivatives thereof, talc, stearic acid or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like; depending on the nature of the active ingredient no carriers are, however, usually required in the case of soft gelatine capsules. Suitable carriers for the production of solutions and syrups are, for example, water, polyols, sucrose, invert sugar, glucose and the like. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, masking agents or antioxidants. They can also contain therapeutically valuable substances other than the compounds of Formula I and their aforementioned pharmaceutically acceptable salts.

Medicaments which contain a compound of Formula I or a pharmaceutically acceptable salt of a basic compound of Formula I with an acid in association with a compatible pharmaceutical carrier material are also an object of the present invention, as is a process for the production of such medicaments which comprises bringing one or more of these compounds or salts and, if desired, one or more other therapeutically valuable substances into a galenical administration form together with a compatible pharmaceutical carrier.

As mentioned earlier, the compounds of Formula I and their aforementioned pharmaceutically acceptable salts can be used in accordance with the invention as therapeutically active substances, especially as antiinflammatory agents or for the prevention of graft rejection following transplant surgery. The dosage can vary within wide limits and will, of course, be fitted to the individual requirements in each particular case. In general, in the case of administration to adults a convenient daily dosage should be about 0.1 mg/kg to about 100 mg/kg, preferably about 0.5 mg/kg to about 5 mg/kg. The daily dosage may be administered as a single dose or in divided doses and, in addition, the upper dosage limit referred to earlier may be exceeded when this is found to be indicated.

Finally, the use of compounds of Formula I and their aforementioned pharmaceutically acceptable salts for the production of medicaments, especially in the treatment or prophylaxis of inflammatory, immunological, oncological, bronchopulmonary, dermatological and cardiovascular disorders, in the treatment of asthma, central nervous system disorders or diabetic complications or for the prevention of graft rejection following transplant surgery, is also an object of the invention.

Methods of Using the Compounds and Compositions

Compounds of Formula I would be useful for, but not limited to, the treatment of any disorder or disease state in a human, or other mammal, which is exacerbated or caused by excessive or unregulated TNF or p38 kinase production by such mammal. Accordingly, the present invention provides a method of treating a cytokine-mediated disease which comprises administering an effective cytokine-interfering amount of a compound of Formula I, or a pharmaceutically acceptable salt or tautomer thereof.

Compounds of Formula I would be useful for, but not limited to, the treatment of inflammation in a subject, and for use as antipyretics for the treatment of fever. Compounds of the invention would be useful to treat arthritis, including but not limited to, rheumatoid arthritis, spondyloarthropathies, gouty arthritis, osteoarthritis, systemic lupus erythematosus and juvenile arthritis, osteoarthritis, gouty arthritis and other arthritic conditions. Such compounds would be useful for the treatment of pulmonary disorders or lung inflammation, including adult respiratory distress syndrome, pulmonary sarcoidosis, asthma, silicosis, and chronic pulmonary inflammatory disease. The compounds are also useful for the treatment of viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpes virus. The compounds are also useful for the treatment of bone resorption diseases, such as osteoporosis, endotoxic shock, toxic shock syndrome, reperfusion injury, autoimmune disease including graft vs. host reaction and allograft rejections, cardiovascular diseases including atherosclerosis, thrombosis, congestive heart failure, and cardiac reperfusion injury, renal reperfusion injury, liver disease and nephritis, and myalgias due to infection.

The compounds are also useful for the treatment of Alzheimer's disease, influenza, multiple sclerosis, cancer, diabetes, systemic lupus erthrematosis (SLE), skin-related conditions such as psoriasis, eczema, burns, dermatitis, keloid formation, and scar tissue formation. Compounds of the invention also would be useful to treat gastrointestinal conditions such as inflammatory bowel disease, Crohn's disease, gastritis, irritable bowel syndrome and ulcerative colitis. The compounds would also be useful in the treatment of ophthalmic diseases, such as retinitis, retinopathies, uveitis, ocular photophobia, and of acute injury to the eye tissue. Compounds of the invention also would be useful for treatment of angiogenesis, including neoplasia; metastasis; ophthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant, conditions such as hemangiomas, including infantile hemangiomas, angiofibroma of the nasopharynx and avascular necrosis of bone; diabetic nephropathy and cardiomyopathy; and disorders of the female reproductive system such as endometriosis. The compounds of the invention may also be useful for preventing the production of cyclooxygenase-2.

Besides being useful for human treatment, these compounds are also useful for veterinary treatment of companion animals, exotic animals and farm animals, including mammals, rodents, and the like. More preferred animals include horses, dogs, and cats.

The present compounds may also be used in co-therapies, partially or completely, in place of other conventional antiinflammatories, such as together with steroids, cyclooxygenase-2 inhibitors, NSAIDs, DMARDS, immunosuppressive agents, 5-lipoxygenase inhibitors, $LTB_4$ antagonists and $LTA_4$ hydrolase inhibitors.

As used herein, the term "TNF mediated disorder" refers to any and all disorders and disease states in which TNF plays a role, either by control of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disorder mediated by TNF.

As used herein, the term "p38 mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, would therefore be considered a disorder mediated by p38.

As TNF-β has close structural homology with TNF-α (also known as cachectin), and since each induces similar biologic responses and binds to the same cellular receptor, the synthesis of both TNF-α and TNF-β are inhibited by the compounds of the present invention and thus are herein referred to collectively as "TNF" unless specifically delineated otherwise.

EXAMPLES

Additional objects, advantages, and novel features of this invention will become apparent to those skilled in the art upon examination of the following illustrative examples thereof, which are not intended to be limiting.

Example 1

Sulfone 1

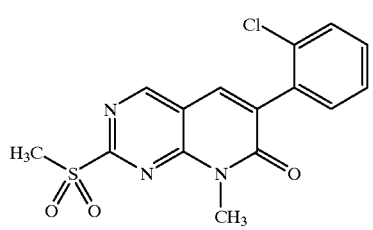

1

This example illustrates the preparation of sulfone 1 from ethyl 4-chloro-2-methylthiopyrimidine-5-carboxylate.

Step 1.1 Preparation of Ethyl 4-methylamino-2-methylthiopyrimidine-5-carboxylate

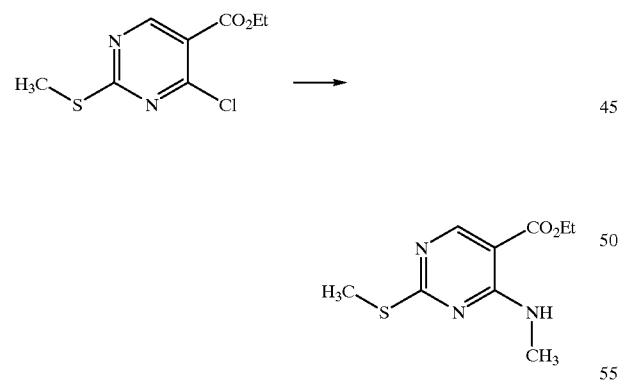

A solution of 20 g (86 mmol) of ethyl 4-chloro-2-methylthiopyrimidine-5-carboxylate (Aldrich Chemical Co., Milwaukee, Wis., USA) in 250 mL of dichloromethane was cooled to 0° C. and treated slowly with 35 mL (281 mmol) of a 33% solution of methylamine in ethanol. After stirring for 30 minutes, 150 mL of water was added and the phases were separated. The organic phase was dried over magnesium sulfate and filtered. The filtrate was evaporated under reduced pressure to give 19 g (97%) of ethyl 4-methylamino-2-methylthiopyrimidine-5-carboxylate as a white solid.

Step 1.2 Preparation of 4-methylamino-2-methylthiopyrimidine-5-methanol

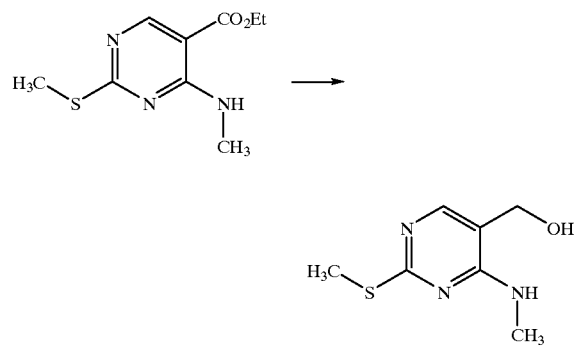

Lithium aluminum hydride (9 g, 237 mmol) was stirred in 300 mL of dry tetrahydrofuran and treated dropwise with a solution of 34 g (143 mmol) of ethyl 4-methylamino-2-methylthio-pyrimidine-5-carboxylate in 300 mL of dry tetrahydrofuran and left to stand for 15 minutes. The mixture was cooled in ice and cautiously treated dropwise with 18 mL of water. Sodium hydroxide solution (36 mL, 2M) was added dropwise, followed by 48 mL of water. The resulting suspension was stirred for 17 hours at room temperature and then filtered. The filter residue was washed twice with 100 mL of ethyl acetate. The filtrate and washings were combined and evaporated under reduced pressure. The residue was suspended in 200 mL of dichloromethane/hexane (2:1) and the solid was filtered and dried to give 23.5 g (86%) of 4-methylamino-2-methylthiopyrimidine-5-methanol as a yellow solid.

Step 1.3 Preparation of 4-methylamino-2-methylthiopyrimidine-5-carboxaldehyde

4-Methylamino-2-methylthiopyrimidine-5-methanol (20 g, 108 mmol) and 1 L of dichloromethane were combined with stirring and treated with 87 g (1 mol) of manganese dioxide. The resulting suspension was stirred for 24 hours and then filtered through a filter aid. The filter residue was washed with 100 mL of dichloromethane and the combined filtrate and washings were evaporated under reduced pressure to give 15.8 g (80%) of 4-methylamino-2-methylthiopyrimidine-5-carboxaldehyde as a white solid.

Step 1.4

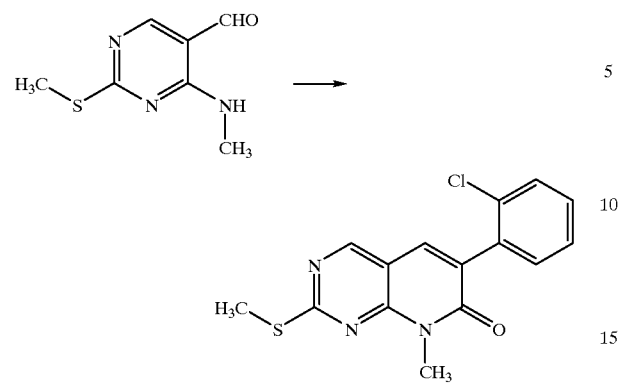

To a mixture of 3.3 g (18.1 mmol) of 4-methylamino-2-methylthiopyrimidine-5-carboxaldehyde, 4.0 g (20.1 mmol) of ethyl-2-chlorophenylacetate in 30 mL of NMP was added 1.5 g of resin, polymer bound 1,3,4,6,7,8-hexahydro-2H pyrimido[1,2-a]pyrimidine. The reaction mixture was heated to 120° C. After 48 h, the reaction mixture was cooled to room temperature and filtered. The resin was washed with NMP and ethyl acetate. The filtrate was diluted with water and filtered. The product was isolated by filtration and by extraction of the filtrate with ethyl acetate. The product was washed with 5% aqueous HCl and water and dried to give 4.0 g of sulfide (mass spec. MH$^+$=318. Mpt. 193.0–193.4).

Step 1.5

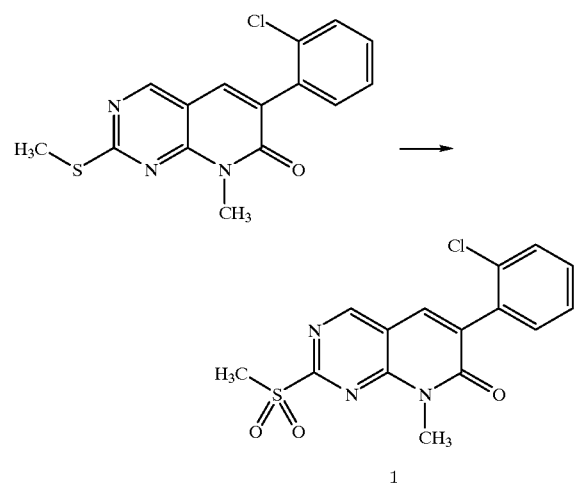

A solution of 13.5 g (42.5 mmol) of sulfide in chloroform was cooled in ice and treated with 20.5 g (91 mmol) of 3-chloroperbenzoic acid. The mixture was stirred at room temperature for 16 hours and diluted with saturated aqueous sodium bicarbonate 20 solution. The phases were separated. The organic phase was dried over magnesium sulfate and filtered. The filtrate was concentrated under reduced pressure and the product was stirred in ethyl ether, filtered and dried to give 13.1 g of sulfone 1 (mass spec. MH$^+$=350. Mpt. 232.6–232.8).

Example 2

Sulfone 2

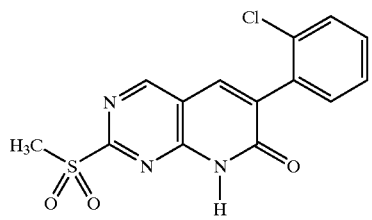

This example illustrates the preparation of 6-(2-chlorophenyl)-2-methanesulfonyl-pyrido[2,3-d]pyrimidin-7-ol starting with ethyl 4-chloro-2-methylthiopyrimidine-5-carboxylate.

Step 2.1 Preparation of Ethyl 4-amino-2-methylthiopyrimidine-5-carboxylate

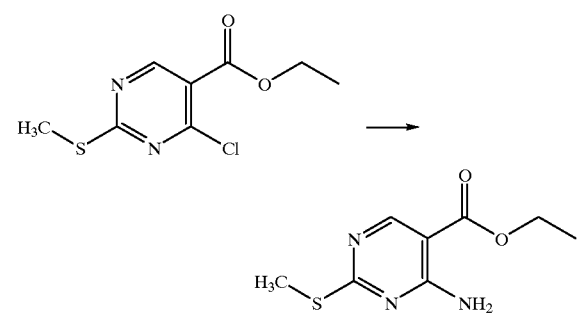

A solution of ethyl 4-chloro-2-methylthiopyrimidine-5-carboxylate (25.4 g, 106 mmol, Aldrich Chemical Co., Milwaukee, Wis., USA) in 300 mL of tetrahydrofuran was treated with 50 mL of triethylamine and 40 mL of aqueous ammonium hydroxide. After stirring for 4 hours, 300 mL of water was added and the phases were separated. The organic layer was washed with 300 mL of brine, concentrated in vacuo, dissolved in methylene chloride, dried over sodium sulfate, filtered and concentrated in vacuo to give 16.5 g (95%) of ethyl 4-amino-2-methylthiopyrimidine-5-carboxylate as a white solid.

Step 2.2 Preparation of 4-amino-2-methylthiopyrimidine-5-methanol

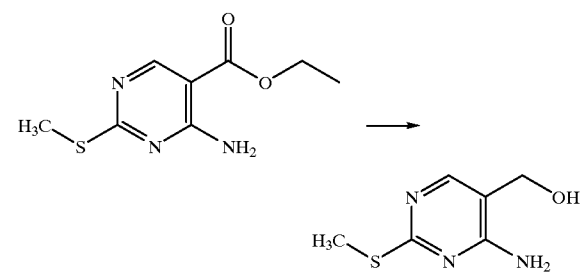

To a 0° C. solution of lithium aluminum hydride (175 mL, 175 mmol) in diethyl ether was added dropwise a solution of 4-amino-2-methylthiopyrimidine-5-carboxylate (34.7 g, 163 mmol) in 500 mL of dry tetrahydrofuran over a period of 1.5 hours. The reaction mixture was slowly warmed to ambient temperature and then cooled back to 0° C. before carefully quenching with 7 mL of water, 7 mL of 2 M sodium hydroxide solution, followed by 14 mL of water. The resulting suspension was filtered and the residue was washed with 2×300 mL of ethyl acetate. The filtrates were combined and concentrated to give 23.0 g (83%) of 4-amino-2-methylthiopyrimidine-5-methanol as a white solid.

Step 2.3 Preparation of 4-amino-2-methylthiopyrimidine-5-carboxaldehyde

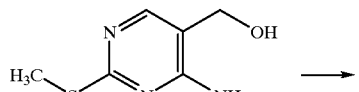

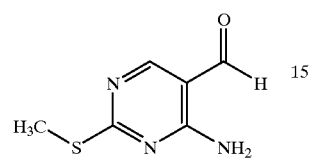

A suspension of 4-amino-2-methylthiopyrimidine-5-methanol (21.8 g, 128 mmol) in 800 mL of methylene chloride was treated with activated manganese oxide powder (63.0 g, 725 mmol). The reaction mixture was stirred for 18 hours, then filtered through a pad of celite. The solid residue was repeatedly washed with a solution of hot methylene chloride and methanol. The filtrates were combined and concentrated to give 17.5 g (81%) of 4-amino-2-methylthiopyrimidine-5-carboxaldehyde as a white solid.

Step 2.4 Preparation of 6-(2-chlorophenyl)-2-methylthio-pyrido[2,3-d]pyrimidin-7-ol

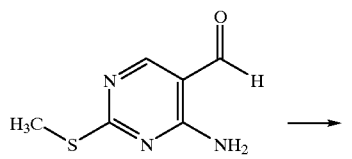

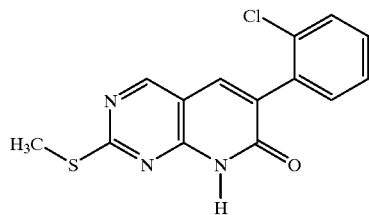

To a solution of 4-amino-2-methylthiopyrimidine-5-carboxaldehyde (21.7 g, 128 mmol) and ethyl-2-chlorophenylacetate (31.3 g, 158 mmol) in 250 mL of dry 1-methyl-2-pyrrolidinone was added potassium carbonate (63.0 g, 491 mmol). The reaction mixture was stirred at 95° C. for 16 hours and monitored by TLC (20:80, ethyl acetate/hexanes). An additional 12.0 g (60 mmol) of ethyl-2-chlorophenylacetate was added and the reaction mixture was stirred at 95° C. for another 16 hours. The reaction mixture was cooled and filtered. The filtered solids were washed with ethyl acetate. The filtrates were combined and diluted with 400 mL of water and 300 mL of ethyl acetate. The phases were separated, and the organic layer was washed with brine, dried over sodium sulfate, filtered and concentrated in vacuo until a yellow precipitate formed. The solids were washed with ethyl acetate and dried to yield a minor amount of product. Most of the product remained in the aqueous layer and slowly precipitated out upon standing. The resulting suspension that formed was filtered and washed with water and ethyl acetate. This procedure was repeated six times yielding a total of 31.9 g (82%) of 6-(2-chlorophenyl)-2-methanesulfonyl-pyrido[2,3-d]pyrimidin-7-ol. Mass spec. $M^+=303$, mp=234.5–235.3° C.

Step 2.5 Preparation of 6-(2-chlorophenyl)-2-methanesulfonyl-pyrido[2,3-d]pyrimidin-7-ol

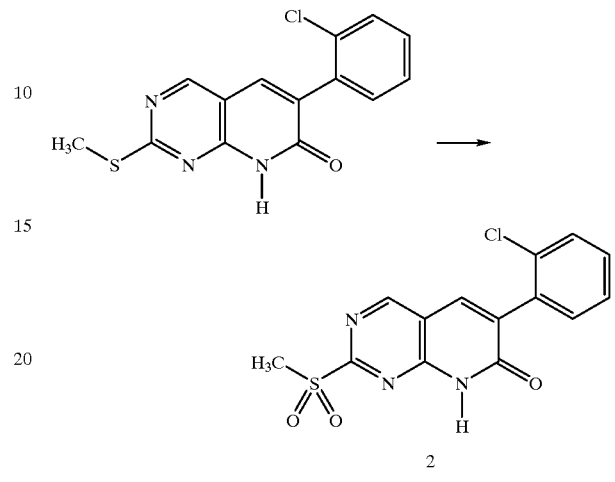

To a solution of 6-(2-chlorophenyl)-2-methylthio-pyrido [2,3-d]pyrimidin-7-ol (25.2 g, 82.9 mmol) was added a slurry of Oxone™ (105 g, 171 mmol) in 200 mL of water. The reaction mixture was stirred for 5 hours, filtered and concentrated in vacuo. The resulting slurry was filtered and the collected solids were successively washed with water four times and dried to give 23.2 g (83%) of 6-(2-chlorophenyl)-2-methanesulfonyl-pyrido[2,3-d]pyrimidin-7-Ol as a light-yellow solid. Mass spec. $MH^+=336$, mp=215.1–221.1° C.

Example 3

This example illustrates the preparation of 6-(2-chlorophenyl)-2-[(1-methyl-piperidin-4-ylmethyl)-amino]-8H-pyrido[2,3-d]pyrimidin-7-one.

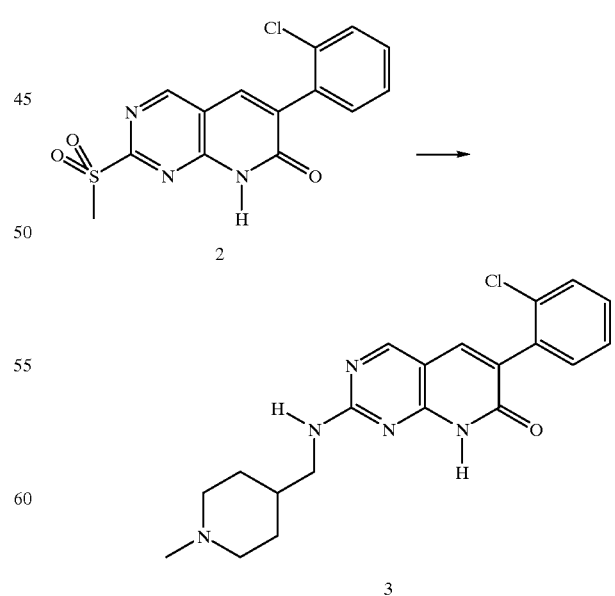

The sulfone 2 (0.5 g, 1.49 mmol) was combined with 1-methyl-4-aminomethylpiperidine (0.57 g, 4.47 mmol).

The mixture was heated to 110° C. and stirred for 2 hours. The reaction was cooled to room temperature and the residue was dissolved in methanol/dichloromethane, and purified by column chromatography on silica gel in 10% methanol/dichloromethane. The fractions containing the product was combined and concentrated. The resulting residue was dissolved in 15 ml of 10% methanol/dichloromethane and treated with 1 equivalent of 1M HCl in ether. The solution was concentrated to a residue and triturated in ether. The solid was filtered and dried to yield 0.25 g of 6-(2-chlorophenyl)-2-[(1-methyl-piperidin-4-ylmethyl)-amino]-8H-pyrido[2,3-d]pyrimidin-7-one, HCl salt. Mass spec. MH$^+$=383, melting pt.=213–220° C.

Example 4

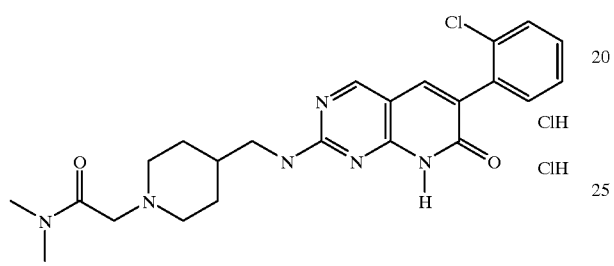

Step 4.1 Preparation of 4B

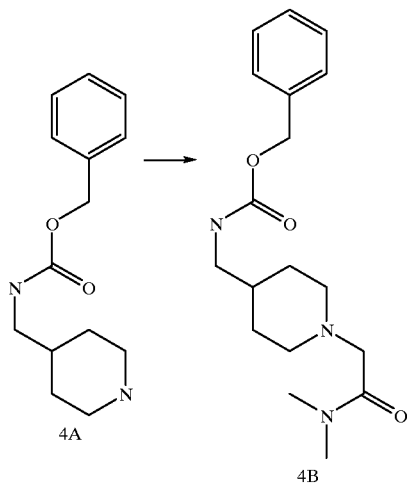

To a solution of compound 4A (4.704 g, 18.94 mmol) in DMF (30 mL) was added sodium carbonate (2.2 g, 1.1 eq) followed by 2-chloro-N,N-dimethyl acetamide (2.14 mL, 1.1 eq). The resulting mixture was stirred vigorously at room temperature for 18 hours. TLC indicated that more than 50% starting material remained so the reaction was heated to 80° C. for an additional 24 hours. Once again, TLC analysis showed that there was a substantial amount of starting material remaining, so the mixture was cooled to room temperature and then additional 2-chloro-N,N-dimethyl acetamide (0.58 mL, 0.3 eq) was added. The reaction was heated to 80° C. for another 4.5 hours whereby analysis by TLC indicated that there was very little starting material remaining. Then, ethyl acetate (150 mL) and water (50 mL) were added, and the mixture was partitioned and the layers were separated. The aqueous layer was further extracted with ethyl acetate (1×50 mL) and the combined organic layers were washed with brine (3×35 mL). The organic layers were combined, dried over magnesium sulfate, filtered and concentrated and dried under vacuum to give 9.9 g of crude product. Purification by flash chromatography using silica gel and gradient elution (neat dichloromethane to 10% methanol in dichloromethane) afforded compound 4B (3.91 g) as a thick syrup. MH$^+$=334.

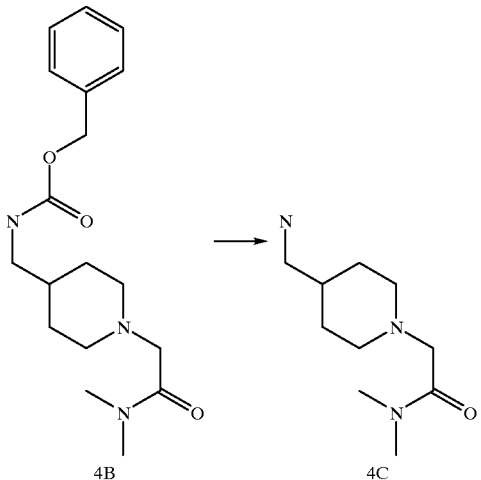

Step 4.2 Preparation of 4C

The compound 4B was taken up in ethanol (120 mL) and nitrogen gas was gently bubbled over the solution for 5 minutes. Then 10% palladium on activated charcoal (1.5 g) was added and the mixture was placed under 1 atmosphere of hydrogen gas and stirred at room temperature for 18 hours. Analysis by TLC indicated that the reaction was complete so the mixture was filtered through a 2.5 cm bed of celite. The filtrate was concentrated and dried under vacuum to afford the compound 4C, 4-aminomethyl-1-dimethylaminocarbonylmethyl-piperidine (2.15 g) as an oil. (M+H)$^+$=200.

Step 4.3 Preparation of 4

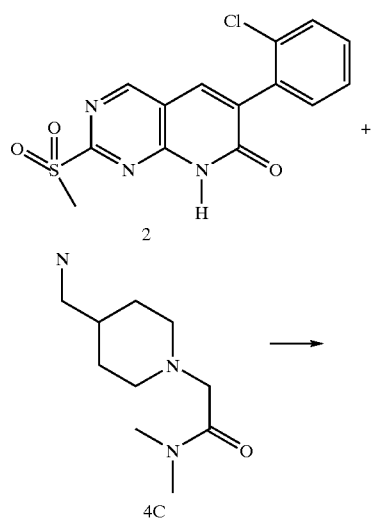

-continued

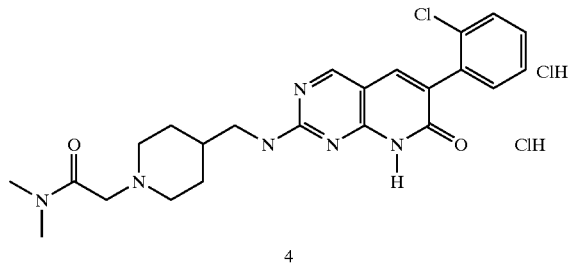

4

The sulfone 2 (200 mg, 0.614 mmol), the compound 4C (367 mg, 3 eq) and N-methyl pyrolidinone (0.3 mL) were mixed in a 10 mL flask and heated at 110° C. with stirring. After 5 minutes, the fluid mixture turned to a solid and by TLC analysis the reaction was complete. The reaction mixture was cooled and methanol (20 mL) was added. The precipitate was crushed up and then filtered to yield a white powder (235 mg). M.p.=263.1–263.5° C., (M+H)$^+$=455. This free amine (230 mg) was dissolved in dichloromethane (50 mL) and methanol (50 mL) and HCl gas was bubbled through the solution for 15 minutes. The vessel was capped tightly and stirred for 2 hours. Then the solvent was removed under reduced pressure at 50° C. and coevaporated with dichloromethane two times. The resulting HCl salt was dried under vacuum at 56° C. for 8 hours to give the compound 4 (276 mg) as an off-white solid. M.p.=211.8–212.8° C., (M+H)$^+$=455 (free base).

Example 5

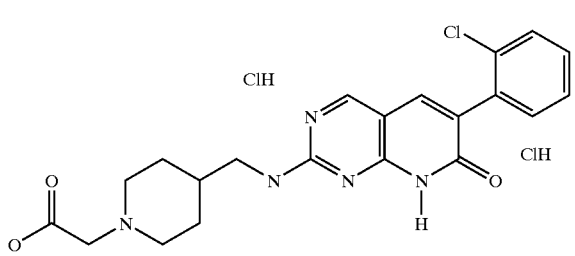

5

Step 5.1 Preparation of 5A

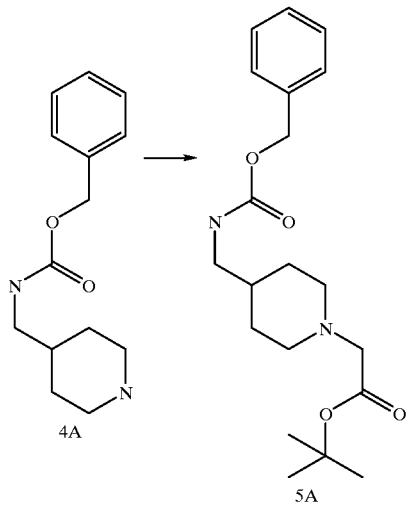

The compound 4A (4.632 g, 18.65 mmol) was dissolved in dimethylformamide (30 mL). To this solution was added sodium carbonate (2.17 g, 1.1 eq) and t-butyl bromoacetate (3 mL, 1.1 eq). The resulting mixture was stirred vigorously at room temperature for 18 hours. TLC analysis showed that very little starting material was present. Ethyl acetate (100 mL) and water (100 mL) were added to the reaction, and the mixture was partitioned and the layers were separated. The aqueous layer was further extracted with ethyl acetate (2×100 mL). The organic layers were combined, washed with water (1×75 mL) and brine (1×75 mL), dried over magnesium sulfate, filtered, concentrated and dried under vacuum to give 6.5 g of the crude product. Purification by flash column chromatography on silica gel using 3% methanol in dichloromethane as the eluent gave 5A (3.95 g) as a thick syrup, (M+H)$^+$=363.

Step 5.2 Preparation of 5B

The compound 5A (3.95 g, 10.9 mmol) was dissolved in ethanol (125 mL) and nitrogen gas was gently passed over the mixture for 5 minutes, then 10% palladium on activated charcoal (1.5 g) was added. The resulting mixture was placed under 1 atmosphere of hydrogen gas and stirred for 18 hours. TLC analysis indicated that the reaction was complete and the reaction was filtered through a 2.5 cm bed of celite. The filtrate was concentrated and dried under vacuum to afford the compound 5B, 4-aminomethyl-1-tert-butyloxycarbonylmethyl-piperidine as a colorless oil (2.26 g). (M+H)$^+$=229.

Step 5.3 Preparation of Compound 5

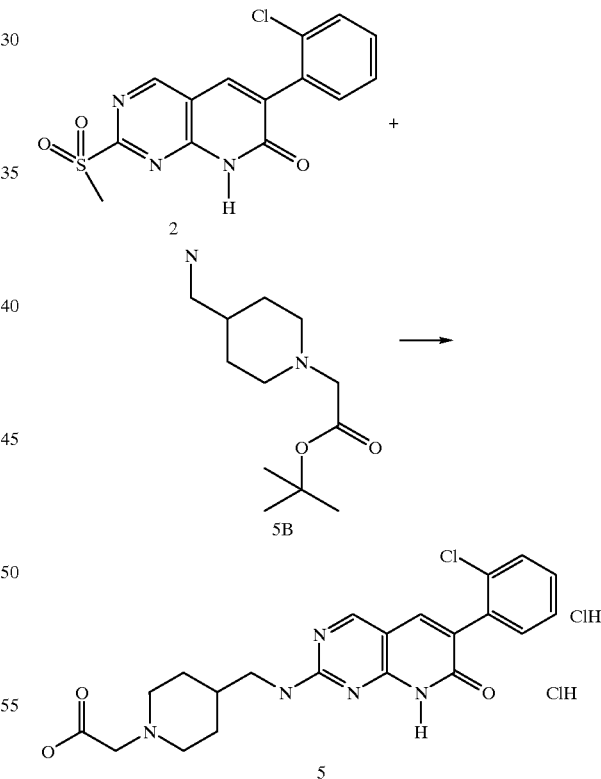

The sulfone 2 (200 mg, 0.614 mmol), compound 5B (420 mg, 3 eq), and N-methyl pyrrolidinone were mixed in a 10 mL flask and heated to 110° C. with stirring. The fluid mixture became semi-solid after about 10 minutes. The mixture was stirred for another 20 minutes and TLC analysis showed that the reaction was complete. Then 15 mL of ethyl acetate and 100 mL hexanes were added to the reaction mixture. The precipitated product was crushed up and filtered to provide a white powder. The powder was washed with 60 mL of hexanes and vacuum dried to yield 270 mg of the free amine t-butyl ester as a white powder. M.p.= 217.6–220.0° C., (M+H)⁺=484. The free amine was dissolved in dioxane (100 mL) and HCl gas was bubbled through the solution for 15 minutes resulting in a homogeneous solution. The vessel was capped tightly and stirred at room temperature for 18 hours. The resulting precipitate was filtered and dried at 56° C. for 8 hours to give the HCl salt 11 (200 mg). M.p.=235.3–237.9° C., (M+H)⁺=428 (free amine carboxylic acid).

Example 6

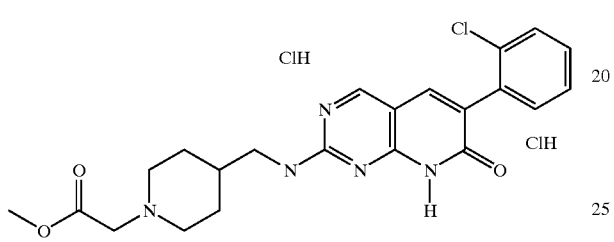

Step 6.1 Preparation of 6A

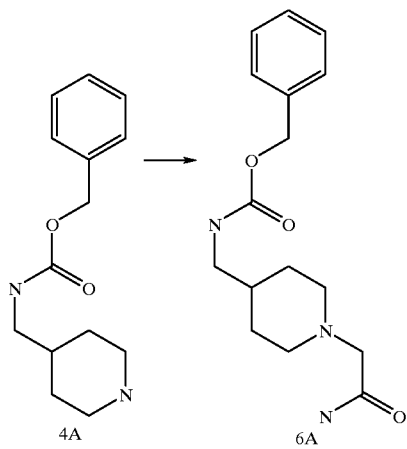

The compound 4A (4.889 g, 19.69 mmol) was dissolved in dimethylformamide (30 mL) and sodium carbonate (2.3 g, 1.1 eq) was added followed by 2-bromoacetamide (2.99 g, 1.1 eq) and the resulting mixture was stirred vigorously at room temperature for 18 hours. Analysis by TLC showed that the reaction was nearly complete. Ethyl acetate (150 mL) and water (50 mL) were added, and the mixture was partitioned and the layers were separated. The organic layer was washed with water (2×50 mL) and brine (1×75 mL), dried over magnesium sulfate, filtered, concentrated and vacuum dried to provide a solid. Hexanes (300 mL) were added to the residue and the solids were crushed up and mixed well. The supernatant was then decanted. This procedure was repeated again with 300 mL of hexanes. The residue was dried under vacuum to give a white powder 6A (3.13 g). (M+H)⁺=306.

Step 6.2 Preparation of 6B

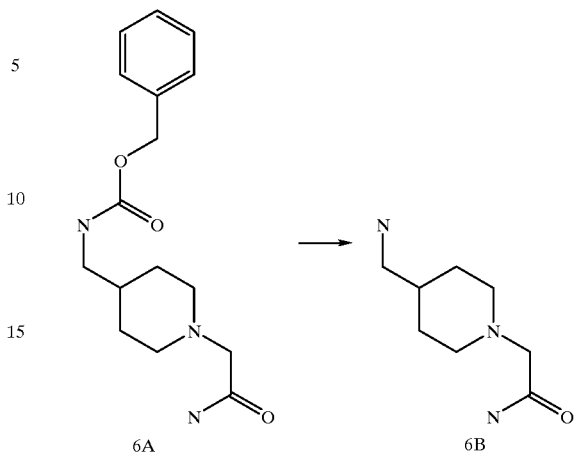

The compound 6A (3.1 g, 10.2 mmol) was dissolved in ethanol (250 mL) and nitrogen gas was gently bubbled through the mixture for 5 minutes. A mixture of 10% palladium on activated carbon (1.45 g) was added. The resulting mixture was placed under 1 atmosphere of hydrogen and stirred for 18 hours. The mixture was filtered through a 2.5 cm bed of celite. The filtrate was concentrated under reduced pressure at 40° C. and dried under vacuum to give the compound 6B (1.77 g) as a sticky white solid. (M+H)⁺=172.

Step 6.3 Preparation of the Compound 6

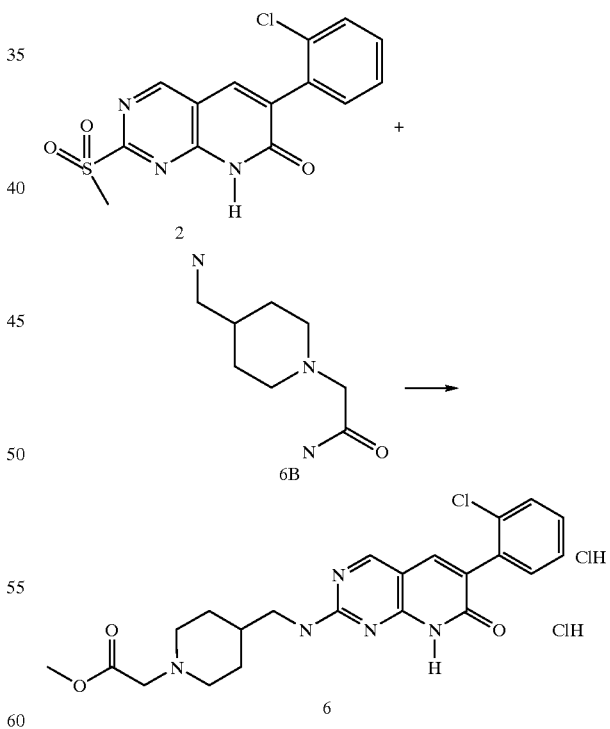

The sulfone 2 (400 mg, 1.23 mmol), the compound 6B (630 mg, 3 eq) and N-methyl pyrrolidinone (0.3 mL) were mixed in a 25 mL flask and the mixture was heated to 110° C. with stirring for 30 minutes. The fluid mixture became a solid and TLC analysis indicated that the reaction was complete. The reaction mixture was diluted with about 20 mL of methanol and the white solid was filtered and dried to give 410 mg of the free amine primary amide. M.p.= 244.6–245.9° C., (M+H)⁺=427. This free amine primary amide was then dissolved in methanol (100 mL) and HCl gas was bubbled through the solution for 10 minutes. The vessel was then capped tightly and stirred at room temperature for 3 days. The solvent was removed under reduced pressure at 40° C. and then 10 mL of methanol was added to the residue. To the resulting solution was added tetrahydrofuran (100 mL) and the precipitate that was formed was filtered and collected to give the compound 6 as an off-white powder (250 mg). M.p.=220.0–221.1° C., (M+H)⁺=442 (free amine, methyl ester).

Example 7

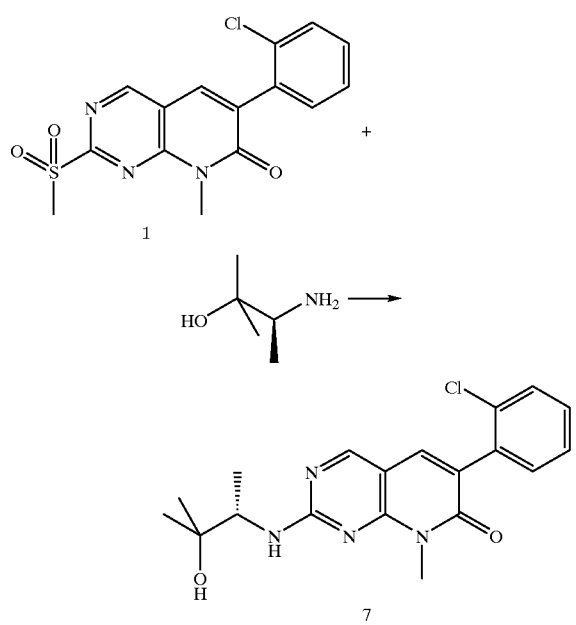

To a solution of the compound 9B (0.28 g, 2 mmol) in acetonitrile (5 mL) at room temperature was added TMSCN (0.8 mL, 3 eq). The resulting mixture was heated to 80° C. with stirring until the mixture was homogeneous. Then, sulfone 1 (0.35 g, 1 mmol) was added and the reaction was stirred at 80° C. for 40 minutes. The reaction was quenched with methanol (10 mL) and stirred for 5 minutes. After concentrating under reduced pressure at 50° C., ethyl acetate (35 mL) and water (25 mL) were added to the residue. The organic layer was separated, washed with water (2×25 mL) and brine (1×25 mL), dried over magnesium sulfate, filtered, concentrated and dried to give 408 mg of crude material. Purification by preparative thin layer chromatography afforded the amine as an off-white powder (299 mg). (M+H)⁺=373, M.P.=91.4–93.2° C. The free amine was dissolved in ethyl acetate (10 mL) and with stirring at room temperature was added a solution of 1M HCl in diethyl ether (1.2 mL, 1.5 eq). After stirring for 30 minutes, the solvent was removed under reduced pressure at 55° C. Further concentration under high vacuum at 56° C. for 6 hours gave compound 7 as an off-white powder (275 mg). (M+H)⁺=373, M.P.=178.0–181.5° C.

Example 8

This example illustrates the preparation of 6-(2-chlorophenyl)-2-[(1,1-dimethyl-2-hydroxyethyl)amino]-8H-pyrido[2,3-d]pyrimidin-7-one.

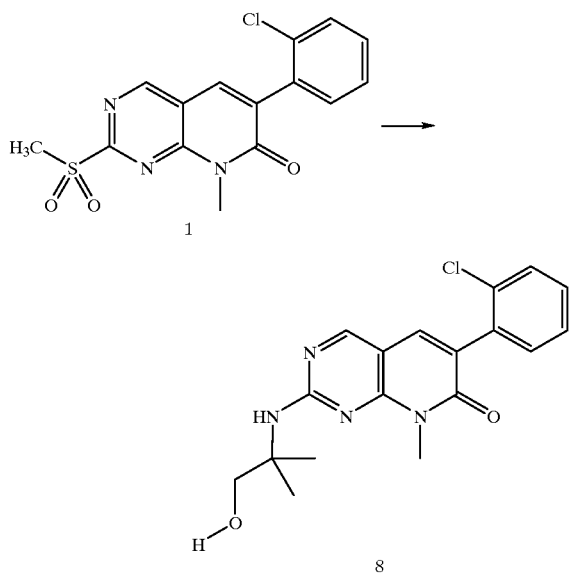

A mixture of 0.350 g (1.0 mmol) of sulfone 1 and 0.445 g (5.0 mmol) was stirred at 120° C. for 1 hour and then cooled to room temperature. The crude product was purified by column chromatography (5% methanol/dichloromethane) to give the desired product as a foam. The residue was suspended in methanol and addition of hydrochloric acid (1.0 M/Et₂O, 1 equivalent), stirred for 20 minutes and concentrated under reduced pressure. The residue was stirred in a mixture of MeOH/Et₂O for 1 hour, and the product was filtered to provide a white solid. Yield 190 mg. Mpt. 228.6–228.9° C. (HCl salt).

Example 9

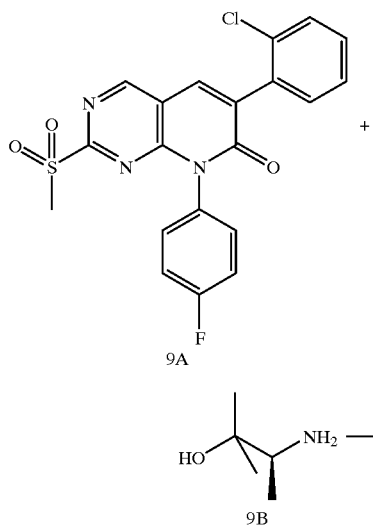

-continued

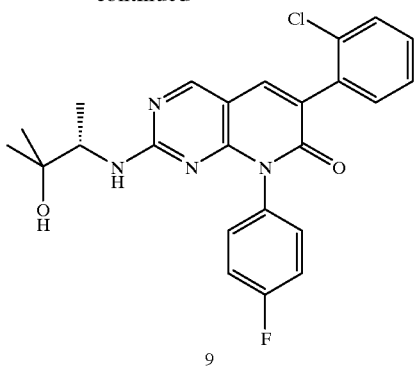

9

To a solution of compound 9B (Chem. Pharm. Bull. 45, 1997, 185–188) (0.28 g, 2 mmol) in acetonitrile (4 mL) at room temperature was added TMSCN (0.8 mL, 3 eq). The resulting mixture was heated to 80° C. until the mixture became homogeneous. Then 9A (0.4 g, 1 mmol) was added to the reaction mixture and stirred at 80° C. for 35 minutes. The reaction mixture was cooled to room temperature and 15 mL of methanol was added and stirred for 5 minutes. The reaction mixture was concentrated under reduced pressure at 50° C. The residue was diluted with ethyl acetate (35 mL) and water (25 mL). The organic phase was separated, washed with water (1×25 mL) and brine (1×25 mL), dried over magnesium sulfate, filtered and concentrated to yield 445 mg of crude material. Purification by preparative thin layer chromatography eluting with 50% ethyl acetate in hexanes gave the free amine as an off-white powder (242 mg). $(M+H)^+=453$, M.P.=204.7–206.0° C. The free amine was dissolved in ethyl acetate (15 mL) at room temperature and a solution of 1M HCl in diethyl ether (0.6 mL, 1.5 eq) was added. The resulting mixture was stirred for 2 hours. The solvent was removed under reduced pressure at 50° C. and the resulting solid was dried under vacuum at 56° C. to give compound 9 as an off-white powder (219 mg). $(M+H)^+=453$, M.P.=142.0–149.0° C.

Example 10

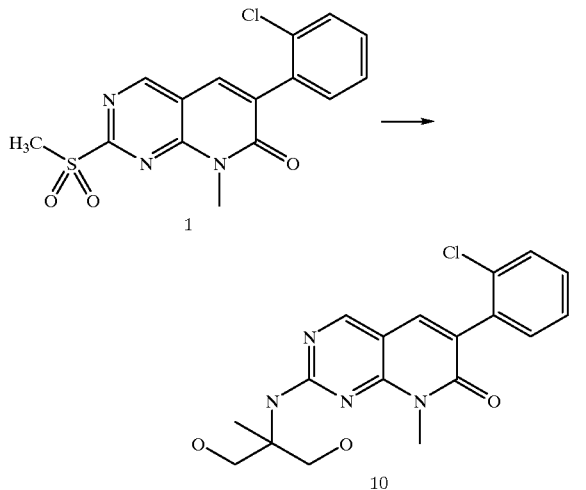

A mixture of sulfone 1 (250 mg, 0.71 mmol) and 2-amino-2-methyl-1,3-propanediol (150 mg, 1.4 mmol) in 1-methyl-2-pyrrolidinone (0.25 mL) was stirred at 80° C. for 12 h and then cooled to room temperature. Water (1 mL) was added and the suspension was stirred for 30 min, filtered and the precipitate was washed with water, dried and suspended in methanol. The suspension was again filtered and dried to give 83 mg of the desired product 10. Mass spec. $MH^+=374$, mpt. 200–210.

Example 11

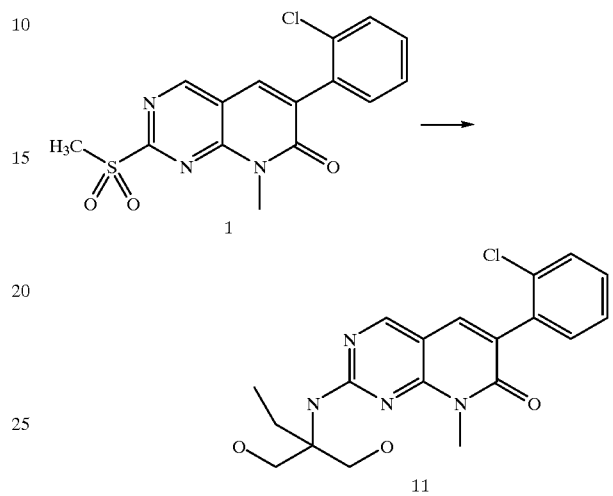

A mixture of sulfone 1 (250 mg, 0.71 mmol) and 2-amino-2-ethyl-1,3-propanediol (170 mg, 1.4 mmol) in 1-methyl-2-pyrrolidinone (0.25 mL) was stirred at 80° C. for 12 h and then cooled to room temperature. Water (1 mL) was added, and the suspension was stirred for 30 min, filtered and the precipitate was washed with water, dried and suspended in methanol. The suspension was again filtered and dried to give 83 mg of the desired product 11. Mass spec. $MH^+=388$, mpt. 98.1–102.

Example 12

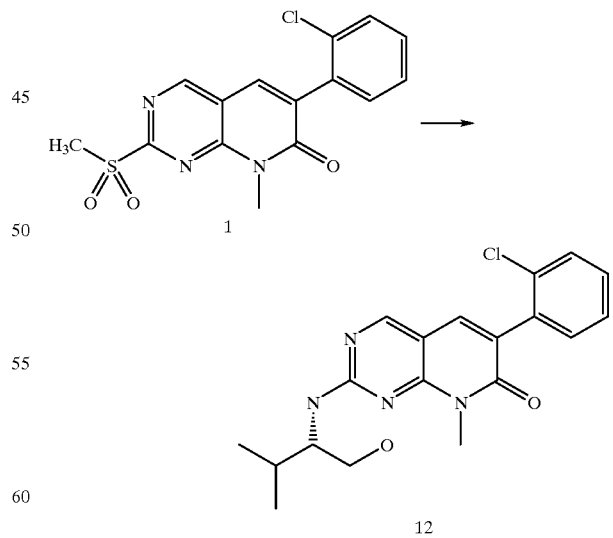

A mixture of sulfone 1 (250 mg, 0.71 mmol) and (S)-(+)-2-amino-3-methyl-1-butanol (147 mg, 1.4 mmol) in 1-methyl-2-pyrrolidinone (0.25 mL) was stirred at 80° C. for 12 h and then cooled to room temperature. Water (1 mL) was added, and the suspension was stirred for 30 min, filtered and the precipitate was washed with water, dried and suspended in methanol. The suspension was again filtered and dried to give 90 mg of the desired product 12. Mass spec. MH$^+$=372, mpt. 167.1–169.1.

Example 13

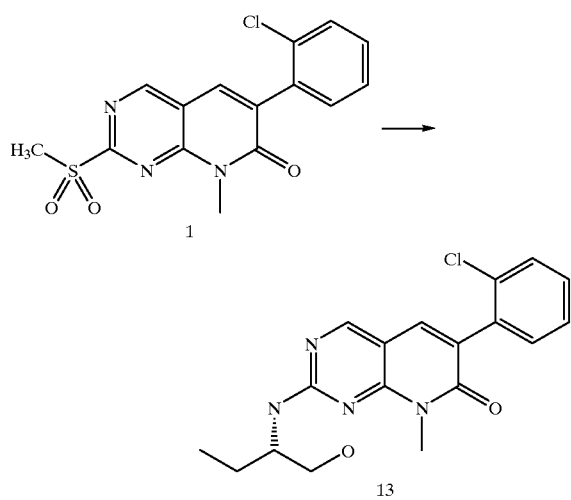

A mixture of sulfone 1 (250 mg, 0.71 mmol) and (S)-(+)-2-amino-1-butanol (127 mg, 1.4 mmol) in 1-methyl-2-pyrrolidinone (0.25 mL) was stirred at 80° C. for 12 h and then cooled to room temperature. Water (1 mL) was added, and the suspension was stirred for 30 min, filtered and the precipitate was washed with water, dried and suspended in methanol. The suspension was again filtered and dried to give 105 mg of the desired product 13. Mass spec. MH$^+$=358, mpt. 170.5–172.1.

Example 14

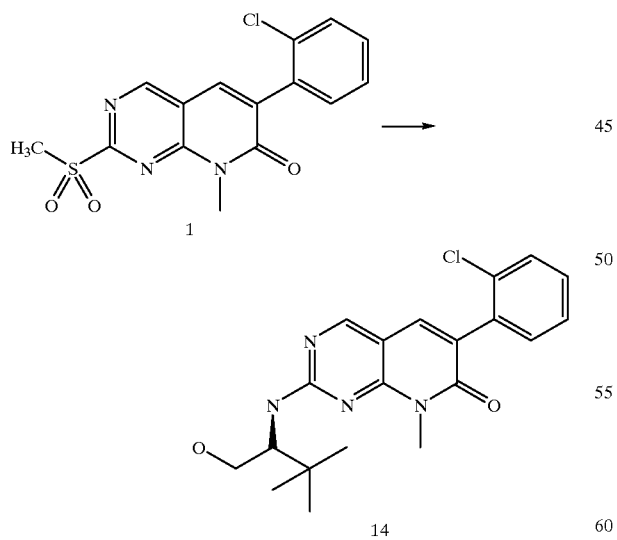

A mixture of sulfone 1 (250 mg, 0.71 mmol) and (S)-tert-leucinol (167 mg, 1.4 mmol) in 1-methyl-2-pyrrolidinone (0.25 mL) was stirred at 80° C. for 12 h and then cooled to room temperature. Water (1 mL) was added, and the suspension was stirred for 30 min, filtered and the precipitate was washed with water, dried and suspended in methanol. The suspension was again filtered and dried to give 116 mg of the desired product 14. Mass spec. MH$^+$=386, mpt. 171.2–174.0.

Example 15

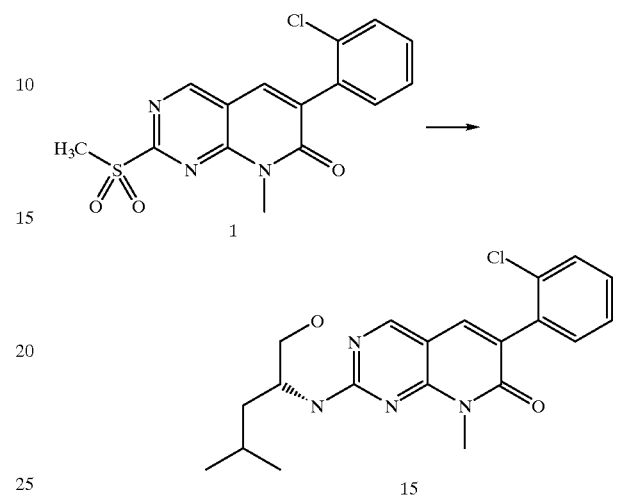

A mixture of sulfone 1 (250 mg, 0.71 mmol) and (R)-(−)-leucinol (167 mg, 1.4 mmol) in 1-methyl-2-pyrrolidinone (0.25 mL) was stirred at 80° C. for 12 h and then cooled to room temperature. Water (1 mL) was added, and the suspension was stirred for 30 min, filtered and the precipitate was washed with water, dried and suspended in methanol. The suspension was again filtered and dried to give 178 mg of the desired product 15. Mass spec. MH$^+$=386, mpt.173.1–176.2.

Example 16

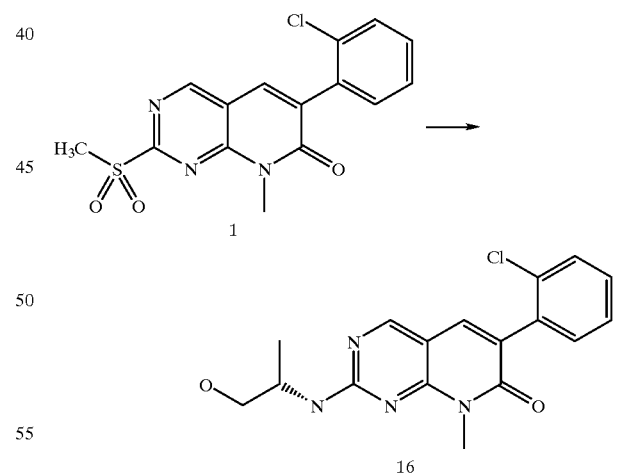

A mixture of sulfone 1 (250 mg, 0.71 mmol) and (S)-(+)-2-amino-1-propanol (107 mg, 1.4 mmol) in 1-methyl-2-pyrrolidinone (0.25 mL) was stirred at 80° C. for 12 h at and then cooled to room temperature. Water (1 mL) was added, and the suspension was stirred for 30 min, filtered and the precipitate was washed with water, dried and suspended in methanol. The suspension was again filtered and dried to give 87 mg of the desired product 16. Mass spec. MH$^+$=344, mpt.131.1–132.2.

Example 17

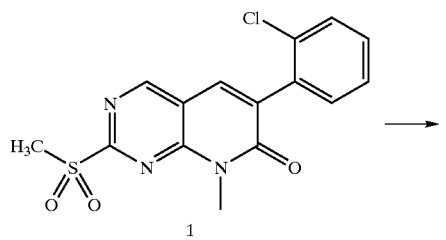

A mixture of sulfone 1 (250 mg, 0.71 mmol) and (S)-(+)-isoleucinol (167 mg, 1.4 mmol) in 1-methyl-2-pyrrolidinone (0.25 mL) was stirred at 80° C. for 12 h and then cooled to room temperature. Water (1 mL) was added, and the suspension was stirred for 30 min, filtered and the precipitate was washed with water, dried and suspended in methanol. The suspension was again filtered and dried to give 200 mg of the desired product 17. Mass spec. MH$^+$=386, mpt.140.1–143.6.

Example 18

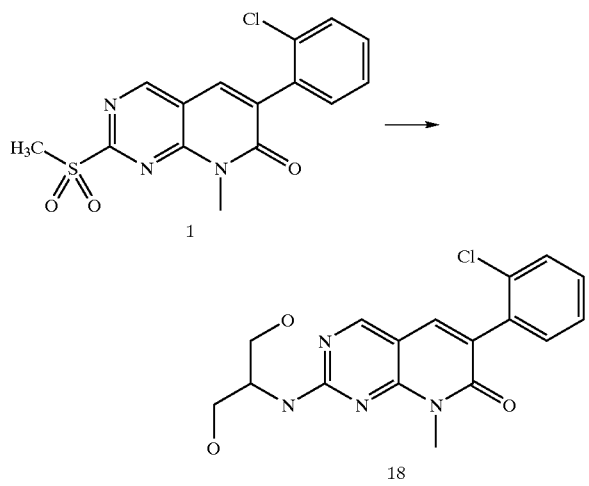

A mixture of sulfone 1 (250 mg, 0.71 mmol) and serinol (130 mg, 1.4 mmol) in 1-methyl-2-pyrrolidinone (0.25 mL) was stirred at 80° C. for 12 h and then cooled to room temperature. Water (1 mL) was added, and the suspension was stirred for 30 min, filtered and the precipitate was washed with water, dried and suspended in methanol. The suspension was again filtered and dried to give 179 mg of the desired product 18. Mass spec. MH$^+$=360, mpt.155.8–157.3.

Example 19

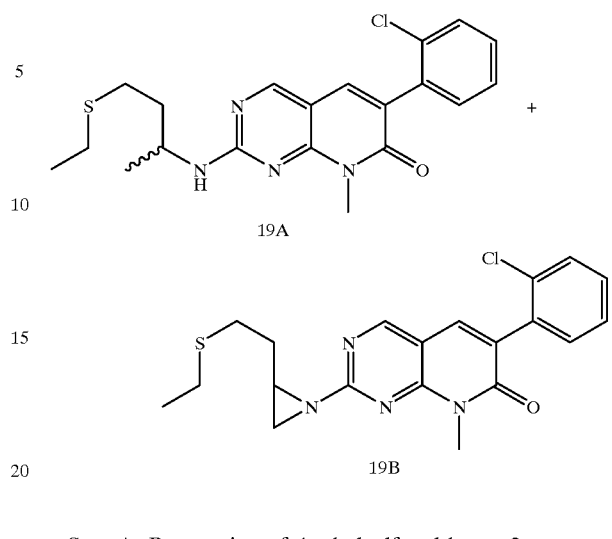

Step A: Preparation of 4-ethylsulfanyl-butan-2-one:

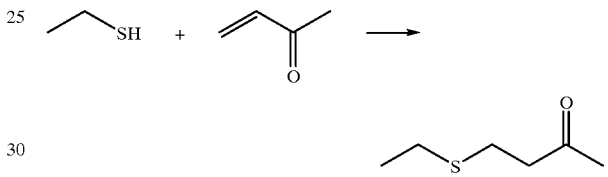

To a solution mixture of ethanethiol (6.2 g, 7.4 mL, 0.1 mol), 3 drops of DBU in 50 mL of THF at 5° C. was added dropwise the methyl vinyl ketone (7.3 g, 8.45 mL, 0.105 mol). The solution mixture was allowed to stir overnight at ambient temperature. The mixture was then concentrated in vacuo to afford 13.6 g of the desired ketone.

Step B: Preparation of 4-ethylsulfanyl-butan-2-one oxime:

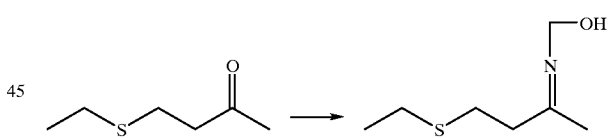

A mixture of the 4-ethylsulfanyl-butan-2-one (13.6 g, 0.1 mol), sodium acetate trihydrate (68 g, 0.5 mol) and hydroxylamine hydrochloride (34.7 g, 0.5 mol) in 500 mL of ethanol was heated to refluxed for 3 hours. The mixture was cooled and concentrated in vacuo. The residue was diluted with water and extracted with ethyl acetate (2×200 mL). The organic solution was then washed with Brine, dried, filtered and concentrated in vacuo to afford 14.7 g of the oxime.

Step C: Preparation of 2-amino-4-ethylsulfanyl-butane:

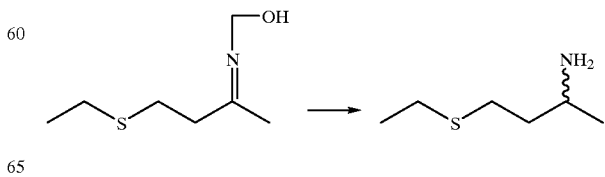

To a solution of lithium aluminum hydride ((1M, 120 mL, 0.12 mol) in tetrahydrofuran at room temperature under a nitrogen atmosphere was added dropwise the 4-ethylsulfanyl-butan-2-one oxime (6 g, 0.04 mol) in 30 mL of tetrahydrofuran. After addition was completed, the mixture was stirred at reflux for 4 hours. The suspension was cooled with an ice-water bath and water (4.6 mL) in 20 mL of tetrahydrofuran was added slowly (dropwise), followed by an aqueous solution of sodium hydroxide (15%, 4.6 mL). Additional water (13.8 mL) was then added and the reaction mixture was stirred for 30 minutes, filtered through a celite pad and rinsed with ethyl acetate (300 mL). The filtrate was dried (brine, MgSO$_4$) and evaporated under reduced pressure affording 3.43 g of the 2-amino-4-ethylsulfanyl-butane (mass spec. M+1=134).

Step D: Preparation of 19A and 19B:

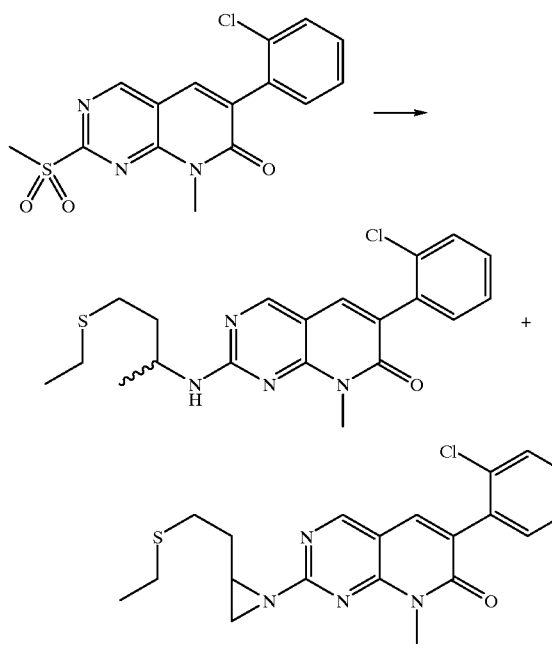

A solution of the sulfone 1 (0.55 g, 1.6 mmol) and 2-amino-4-ethylsulfanyl-butane (0.63 g, 4.8 mmol) in 10 mL of tetrahydrofuran was refluxed for 1 hour. The solution was cooled and concentrated in vacuo and the product was purified by column chromatography with silica eluting with 5% ethyl acetate in dichloromethane affording 421 mg of a racemic mixture of 19A (mass spec. M+1=403) and 31 mg of the aziridine compound 19B (mass spec. M+1=401, MP=160–167° C.).

Example 20

This example illustrates an alternative method for producing 6-(2-chlorophenyl)-8-methyl-2-methylthio-8-hydropyridino[2,3-d]pyrimdin-7-one (VI)

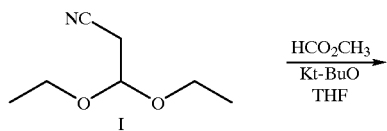

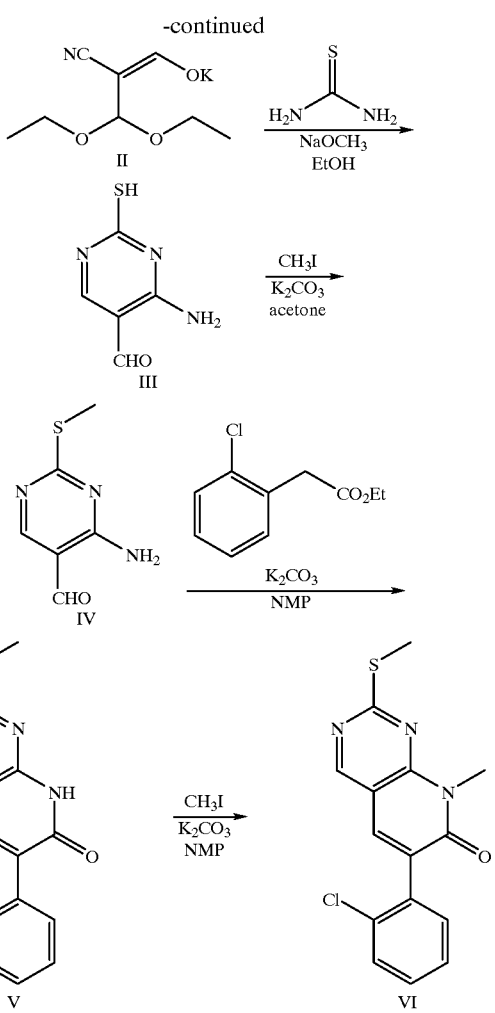

Preparation of 3,3-Diethoxy-2-formylpropionitrile Potassium Salt (II)

To a stirred solution of 3,3-diethoxypropane-nitrile (I, 283.80 g, 1.98 moles) and methyl formate (148.80 g, 2.48 moles) in anhydrous THF (1.1 L) at 10° C. was added 1.0 M potassium tert-butoxide in THF (2.2 L, 2.2 moles). Temperature was maintained in the range of 10° C. to 15° C. throughout the 45 minute addition. Following the addition, the resulting slurry was stirred 2 hours at ambient room temperature. Hexane (400 mL) was then added and stirring was continued for another 20 min. The slurry was filtered and the cake washed with 1/1 hexanes/THF and dried overnight at 60° C. in a vacuum oven. The yield of pale tan powder was 302.5 grams (73.0%). $^1$H-NMR (CD$_3$OD) was consistent with the desired structure II.

Preparation of 4-Amino-2-sulfanylpyrimidine-5-carbaldehyde (III)

A slurry of thiourea (92.8 g, 1.22 moles) in ethanol (90 mL) was heated under reflux and vigorously stirred. To this slurry was added a suspension of 3,3-diethoxy-2-formylpropionitrile potassium salt II (222.20 g, 1.06 moles) in 25% sodium methoxide/methanol (85.5 mL, 0.37 mole) and ethanol (285 mL) in five aliquots over a 10 minute period while maintaining reflux conditions (alternatively, the latter slurry may be heated to 50° C. to give a homogenous solution for the addition). An additional portion of ethanol (150 mL) was added to facilitate stirring. The thick slurry became a bright yellow color following the addition and was held under reflux for an additional 1 hour. The mixture was then cooled and evaporated to near dryness on a rotoevaporator. The residue was dissolved in water (940 mL). Crude product was precipitated from solution by the addition of 30% acetic acid (280 mL) and isolated via filtration using a medium frit sintered glass filtration funnel. The cake was washed with water (800 mL). Purification via trituration in hot water (1 L) for 30 minutes, followed by cooling and filtration gave 118.9 grams (72.3%) of product as a bright yellow solid after drying overnight at 60° C. in a vacuum oven (subsequent preparations have demonstrated that this trituration is unnecessary). An HPLC gave purity as 98.67%. $^1$H-NMR (DMSO-$d_6$) was consistent with desired structure III.

Preparation of 4-Amino-2-methylthiopyrimidine-5-carbaldehyde (IV)

To a solution of 4-amino-2-sulfanyl-pyrimidine-5-carbaldehyde III (100.00 g, 644.4 mmoles) and 325 mesh potassium carbonate (178.10 g, 1.29 moles) in acetone (1.5 L) was added iodomethane (128.10 g, 902.2 mmoles) dropwise over 20 minutes with mild cooling. The mixture was stirred at ambient room temperature over the weekend. TLC showed remaining III and an additional aliquot of iodomethane was added (8 mL) and stirring was continued overnight. TLC again showed some III remaining and an addition portion of iodomethane was added (8 mL) and stirring was continued another 24 hour period. An HPLC showed 95.9% S-alkylated product and 3.7% of compound III. The reaction mixture was stripped to near dryness on a rotoevaporator. Water (1 L) was added to the residue and the product was collected via filtration and washed with water (200 mL). The product was dried overnight in a vacuum oven at 60° C. Yield was 103.37 grams (94.8%). An HPLC showed 95.8% IV and 4.2% III.

Preparation of 6-(2-chlorophenyl)-2-methylthio-8-hydropyridino[2,3-d]pyrimidin-7-one (V)

A mixture of IV (10.00 g, 59.1 mmoles), ethyl 2-(2-chlorophenyl)acetate (14.40 g, 71.8 mmoles), NMP (115 mL) and 325 mesh potassium carbonate (29.00 g, 209.8 mmoles) was heated at 95° C. overnight. The reaction mixture was cooled and diluted with water (800 mL). The resulting slurry was stirred overnight and filtered to isolate product (V). The filter cake was washed with water and dried at 60° C. in a vacuum oven overnight. Isolated yield was 14.9 grams (83.0%) of dark tan solid. Analysis by an HPLC showed 98.3% purity.

Preparation of 6-(2-Chlorophenyl)-8-methyl-2-methylthio-8-hydropyridino[2,3-d]pyrimidin-7-one (VI)

A mixture of V (0.25 g, 0.82 mmole), NMP (5 mL), potassium carbonate (0.11 g, 0.82 mmole), and iodomethane (0.14 g, 0.96 mmole) was stirred under nitrogen at ambient room temperature overnight. Water (15 mL) was added and stirring was continued for 24 hours. The slurry was filtered and the filter cake washed with water (10 mL). An HPLC showed 97.8% purity.

Example 21

This example illustrate an assay protocol for determining in vitro inhibition of p-38 (MAP) Kinase.

The p-38 MAP kinase inhibitory activity of compounds of this invention in vitro was determined by measuring the transfer of the γ-phosphate from γ-$^{33}$P-ATP by p-38 kinase to Myelin Basic Protein (MBP), using the a minor modification of the method described in Ahn, N. G.; et al. *J. Biol. Chem.* Vol. 266(7), 4220–4227, (1991).

The phosphorylated form of the recombinant p38 MAP kinase was expressed with SEK-1 and MEKK in *E. Coli* and then purified by affinity chromatography using a Nickel column.

The phosphorylated p38 MAP kinase was diluted in kinase buffer (20 mM 3-(N-morpholino)propanesulfonic acid, pH 7.2, 25 mM β-glycerol phosphate, 5 mM ethylene glycol-bis(beta-aminoethyl ether)-N,N,N',N'-tetraacetic acid, 1 mM sodium vanadate, 1 mM dithiothreitol, 40 mM magnesium chloride). Test compound dissolved in DMSO or only DMSO (control) was added and the samples were incubated for 10 min at 30° C. The kinase reaction was initiated by the addition of a substrate cocktail containing MBP and γ-$^{33}$P-ATP. After incubating for an additional 20 min at 30° C., the reaction was terminated by adding 0.75% phosphoric acid. The phosphorylated MBP was then separated from the residual γ-$^{33}$P-ATP using a phosphocellulose membrane (Millipore, Bedford, Mass.) and quantitated using a scintillation counter (Packard, Meriden, Conn.).

Compounds of the invention were active in this assay. The p-38 inhibitory activities (expressed as $IC_{50}$, the concentration causing 50% inhibition of the p-38 enzyme being assayed) of some compounds of the invention are:

| CPD # (from Table 1) | $IC_{50}$, μM |
| --- | --- |
| 1 | 0.052 |
| 3 | 2.196 |
| 4 | 6.266 |
| 7 | 0.0003 |
| 8 | 0.031 |
| 10 | 0.042 |
| 11 | 0.024 |
| 12 | 0.124 |
| 13 | 0.048 |
| 18 | 0.092 |

Example 22

This example illustrates an in vitro assay to evaluate the inhibition of LPS-induced TNF-α production in THP1 cells.

The ability of the compounds of this invention to inhibit the TNF-α release was determined using a minor modification of the methods described in Blifeld, et al. *Transplantation*, 51:498–503 (1991).

(a) Induction of TNF Biosynthesis

THP-1 cells were suspended in culture medium [RPMI (Gibco-BRL, Gailthersburg, Md.) containing 15% fetal bovine serum, 0.02 mM 2-mercaptoethanol], at a concentration of 2.5×10$^6$ cells/mL and then plated in 96 well plate (0.2 mL aliquots in each well). Test compounds were dissolved in DMSO and then diluted with the culture medium such that the final DMSO concentration was 5%. Twenty five μL aliquots of test solution or only medium with DMSO (control) were added to each well. The cells were incubated for 30 min., at 37° C. LPS (Sigma, St. Louis, Mo.) was added to the wells at a final concentration of 0.5 μg/ml, and cells were incubated for an additional 2 h. At the end of the incubation period, culture supernatants were collected and the amount of TNF-α present was determined using an ELISA assay as described below.

(b) ELISA Assay

The amount of human TNF-α present was determined by a specific trapping ELISA assay using two anti-TNF-α antibodies (2TNF-H12 and 2TNF-H34) described in Reimund, J. M., et al. *GUT.* Vol. 39 (5), 684–689 (1996).

Polystyrene 96-well plates were coated with 50 μl per well of antibody 2TNF-H12 in PBS (10 μg/mL) and incubated in a humidified chamber at 4° C. overnight. The plates were washed with PBS and then blocked with 5% nonfat-dry milk in PBS for 1 hour at room temperature and washed with 0.1% BSA (bovine serum albumin) in PBS.

TNF standards were prepared from a stock solution of human recombinant TNF-α (R&D Systems, Minneapolis, Minn.). The concentration of the standards in the assay began at 10 ng/mL followed by 6 half log serial dilutions.

Twenty five μL aliquots of the above culture supernatants or TNF standards or only medium (control) were mixed with 25 μL aliquots of biotinylated monoclonal antibody 2TNF-H34 (2 μg/mL in PBS containing 0.1% BSA) and then added to each well. The samples were incubated for 2 hr at room temperature with gentle shaking and then washed 3 times with 0.1% BSA in PBS. 50 μl of peroxidase-streptavidin (Zymed, S. San Francisco, Calif.) solution containing 0.416 μg/mL of peroxidase-streptavidin and 0.1% BSA in PBS was added to each well. The samples were incubated for an additional 1 hr at room temperature and then washed 4 times with 0.1% BSA in PBS. Fifty μL of O-phenylenediamine solution (1 μg/mL O-phenylene-diamine and 0.03% hydrogen peroxide in 0.2M citrate buffer pH 4.5) was added to each well and the samples were incubated in the dark for 30 min., at room temperature. Optical density of the sample and the reference were read at 450 nm and 650 nm, respectively. TNF-α levels were determined from a graph relating the optical density at 450 nm to the concentration used.

The $IC_{50}$ value was defined as the concentration of the test compound corresponding to half-maximal reduction in 450 nm absorbance.

Example 23

This example illustrates an in vivo assay to evaluate the inhibition of LPS-induced TNF-α production in mice (or rats).

The ability of the compounds of this invention to inhibit the TNF-α release, in vivo, was determined using a minor modification of the methods described in described in Zanetti, et. al., *J. Immunol.*, 148:1890 (1992) and Sekut, et. al., *J. Lab. Clin. Med.*, 124:813 (1994).

Female BALB/c mice weighing 18–21 grams (Charles River, Hollister, Calif.) were acclimated for one week. Groups containing 8 mice each were dosed orally either with the test compounds suspended or dissolved in an aqueous vehicle containing 0.9% sodium chloride, 0.5% sodium carboxymethyl-cellulose, 0.4% polysorbate 80, 0.9% benzyl alcohol (CMC vehicle) or only vehicle (control group). After 30 min., the mice were injected intraperitoneally with 20 μg of LPS (Sigma, St. Louis, Mo.). After 1.5 h, the mice were sacrificed by $CO_2$ inhalation and blood was harvested by cardiocentesis. Blood was clarified by centrifugation at 15,600×g for 5 min., and sera were transferred to clean tubes and frozen at −20° C. until analyzed for TNF-α by ELISA assay (Biosource International, Camarillo, Calif.) following the manufacturer's protocol.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All publications, patents, and patent applications cited herein are hereby incorporated by reference in their entirety for all purposes.

What is claimed is:

1. A compound of the formula:

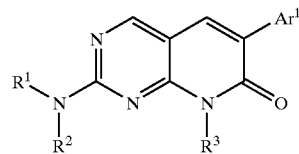

a prodrug or a salt thereof,
wherein:
$R^1$ is hydrogen or alkyl;
$R^2$ is $R^x$—S—$R^y$— (where $R^x$ is alkyl and $R^y$ is alkylene), alkoxy-substituted alkyl, heterocyclylalkyl or $C_4$–$C_5$ cycloalkyl; or
$R^1$ and $R^2$ together with the nitrogen atom to which they are attached form a heterocyclyl group;
$R^3$ is hydrogen, alkyl, amino, monoalkylamino, dialkylamino, cycloalkyl, aryl, aralkyl, haloalkyl, heteroalkyl, cyanoalkyl, alkylene—C(O)—R (where R is hydrogen, alkyl, hydroxy, alkoxy, amino, monoalkylamino or dialkylamino) or acyl; and
$Ar^1$ is aryl.

2. The compound of claim 1 wherein $Ar^1$ is an optionally substituted phenyl.

3. The compound of claim 2, wherein $Ar^1$ is a phenyl group independently substituted with one or two halo, alkyl or methoxy groups.

4. The compound of claim 3, wherein $Ar^1$ is 2-chlorophenyl, 2-methylphenyl or 2-methoxyphenyl.

5. The compound according to claim 4 of the formula:

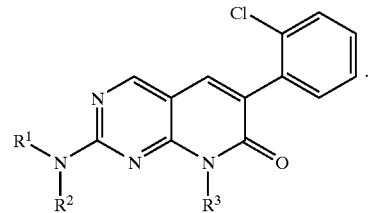

6. The compound according to claim 5, wherein $R^1$ is hydrogen or methyl.

7. The compound according to claim 6, wherein $R^2$ is a substituted piperidinylmethyl.

8. A composition comprising:
(a) an excipient; and
(b) a compound of the formula:

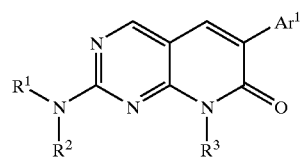

a prodrug or a pharmaceutically acceptable salt thereof, wherein $R^1$ is hydrogen or alkyl;

$R^2$ is $R^x$—S—$R^y$— (where $R^x$ is alkyl and $R^y$ is alkylene), alkoxy-substituted alkyl, heterocyclylalkyl or $C_4$–$C_5$ cycloalkyl; or $R^1$ and $R^2$ together with the nitrogen atom to which they are attached form a heterocyclyl group;

$R^3$ is hydrogen, alkyl, amino, monoalkylamino, dialkylamino, cycloalkyl, aryl, aralkyl, haloalkyl, heteroalkyl, cyanoalkyl, alkylene-C(O)—R (where R is hydrogen, alkyl, hydroxy, alkoxy, amino, monoalkylamino or dialkylamino) or acyl; and $Ar^1$ is aryl.

9. A method for preparing a compound of claim 1, comprising the steps of contacting a compound of the formula Ig:

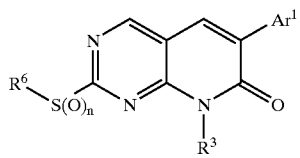

with an amine of the formula $R^1R^2NH$ under conditions sufficient to produce a compound of Formula I:

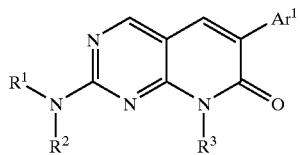

wherein:

$R^1$, $R^2$, $R^3$ and $Ar^1$ are those defined in claim 1;

L is a leaving group;

n is an integer from 0 to 2; and $R^6$ is an alkyl group.

10. The method of claim 9, wherein n is 1.

11. The method of claim 9 wherein n is 2.

12. A method for treating arthritis, Crohn's disease or inflammatory bowel disease comprising administering to a patient in need of such treatment, an effective amount of a compound of claim 1.

13. The compound according to claim 7, wherein the substituted piperidinylmethyl is selected from the group consisting of:

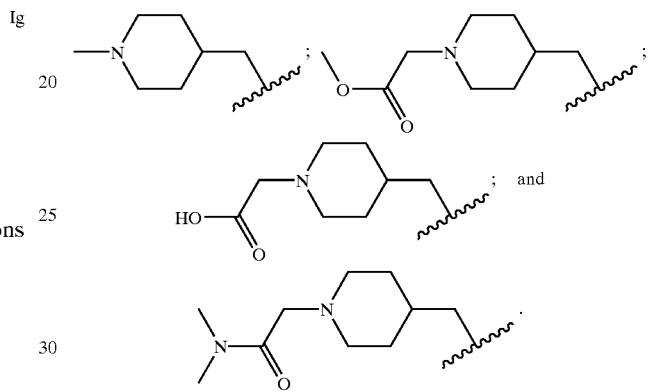

* * * * *

UNITED STATES PATENT AND TRADEMARK OFFICE
CERTIFICATE OF CORRECTION

PATENT NO.  : 6,518,276 B2
DATED       : February 11, 2003
INVENTOR(S) : Arzeno et al.

It is certified that error appears in the above-identified patent and that said Letters Patent is hereby corrected as shown below:

Column 17,
Replace compound 25:

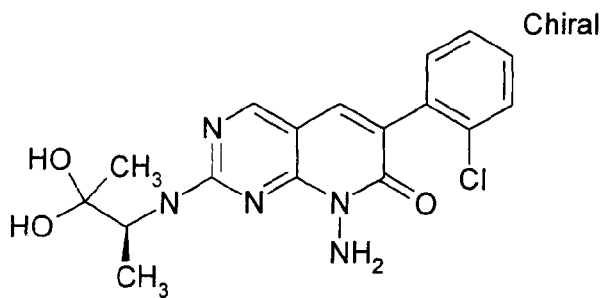

with the corrected compound 25 structure:

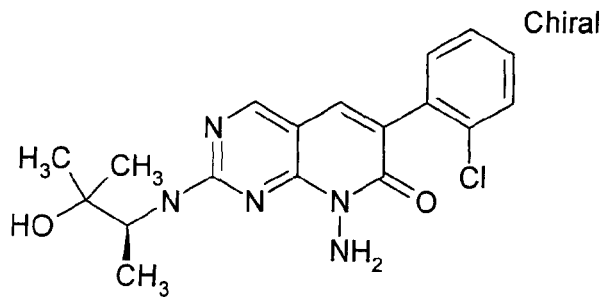

Signed and Sealed this

Twentieth Day of December, 2005

JON W. DUDAS
*Director of the United States Patent and Trademark Office*